US012617758B2

(12) United States Patent
Hah et al.

(10) Patent No.: US 12,617,758 B2
(45) Date of Patent: May 5, 2026

(54) QUINAZOLINE DERIVATIVE HAVING FLT3 INHIBITORY ACTIVITY, AND USE THEREOF

(71) Applicant: INDUSTRY-UNIVERSITY COOPERATION FOUNDATION HANYANG UNIVERSITY ERICA CAMPUS, Ansan-si (KR)

(72) Inventors: Jung-Mi Hah, Ansan-si (KR); Da Seul Im, Ansan-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 497 days.

(21) Appl. No.: 18/245,737

(22) PCT Filed: Sep. 24, 2021

(86) PCT No.: PCT/KR2021/012997
§ 371 (c)(1),
(2) Date: Mar. 17, 2023

(87) PCT Pub. No.: WO2022/065894
PCT Pub. Date: Mar. 31, 2022

(65) Prior Publication Data

US 2023/0357164 A1 Nov. 9, 2023

(30) Foreign Application Priority Data

Sep. 25, 2020 (KR) ........................ 10-2020-0124692

(51) Int. Cl.
*C07D 401/04* (2006.01)
*C07D 239/72* (2006.01)
(Continued)

(52) U.S. Cl.
CPC ......... *C07D 239/74* (2013.01); *C07D 239/72* (2013.01); *C07D 401/04* (2013.01);
(Continued)

(58) Field of Classification Search
None
See application file for complete search history.

(56) References Cited

U.S. PATENT DOCUMENTS

2008/0207617 A1 8/2008 Miwa et al.
2016/0194291 A1 7/2016 Baska et al.
2022/0315573 A1 10/2022 Hah et al.

FOREIGN PATENT DOCUMENTS

KR 102085692 B1 3/2020
WO 2004030671 A2 4/2004

OTHER PUBLICATIONS

English translation of International Search Report corresponding to International Patent Application No. PCT/KR2021/012997 (3 pages) (mailed Dec. 31, 2021).

(Continued)

*Primary Examiner* — Jennifer A Berrios
*Assistant Examiner* — Sophia Reilly
(74) *Attorney, Agent, or Firm* — Myers Bigel, P.A.

(57) ABSTRACT

The present invention relates to a novel quinazoline derivative having fms-like tyrosine kinase 3 (FLT3) inhibitory activity, and a use thereof. A novel quinazoline derivative or a pharmaceutically acceptable salt thereof, according to the present invention, exhibits excellent inhibitory activity against FLT3, and thus targeted treatment through more fundamental approaches is expected in the prevention or treatment of acute myeloid leukemia (AML).

13 Claims, 1 Drawing Sheet

(51) Int. Cl.
*C07D 239/74* (2006.01)
*C07D 401/12* (2006.01)
*C07D 403/04* (2006.01)
*C07D 403/10* (2006.01)
*C07D 405/10* (2006.01)
*C07D 413/04* (2006.01)
*C07D 413/12* (2006.01)
*C07D 413/14* (2006.01)

(52) U.S. Cl.
CPC ......... *C07D 401/12* (2013.01); *C07D 403/04* (2013.01); *C07D 403/10* (2013.01); *C07D 405/10* (2013.01); *C07D 413/04* (2013.01); *C07D 413/12* (2013.01); *C07D 413/14* (2013.01)

(56) References Cited

OTHER PUBLICATIONS

Im et al. "Discovery of 5-methyl-N-(2-arylquinazolin-7-yl)isoxazole-4-carboxamide analogues as highly selective FLT3 inhibitors" Journal of Enzyme Inhibition and Medicinal Chemistry, 35(1):1110-1115 (2020).

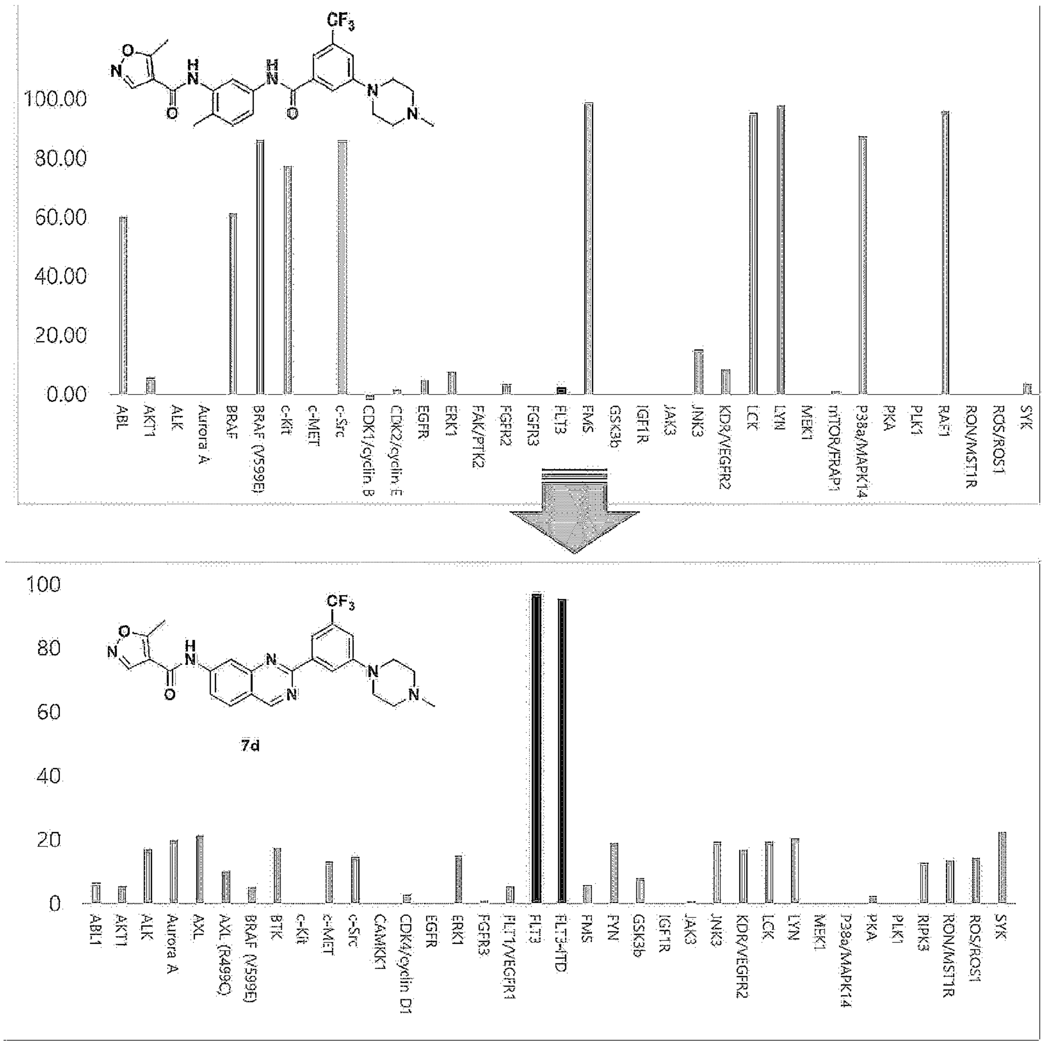
100.00
80.00
60.00
40.00
20.00
0.00
ABL
AKT1
ALK
Aurora A
BRAF
BRAF (V599E)
c-Kit
c-MET
c-Src
CDK1/cyclin B
CDK2/cyclin E
EGFR
ERK1
FAK/PTK2
FGFR2
FGFR3
FLT3
FMS
GSK3b
IGF1R
JAK3
JNK3
KDR/VEGFR2
LCK
LYN
MEK1
mTOR/FRAP1
P38a/MAPK14
PKA
PLK1
RAF1
RON/MST1R
ROS/ROS1
SYK
100
80
60
40
20
0
7d
ABL1
AKT1
ALK
Aurora A
AXL
AXL (R499C)
BRAF (V599E)
BTK
c-Kit
c-MET
c-Src
CAMKK1
CDK4/cyclin D1
EGFR
ERK1
FGFR3
FLT1/VEGFR1
FLT3
FLT3-ITD
FMS
FYN
GSK3b
IGF1R
JAK3
JNK3
KDR/VEGFR2
LCK
LYN
MEK1
P38a/MAPK14
PKA
PLK1
RIPK3
RON/MST1R
ROS/ROS1
SYK

QUINAZOLINE DERIVATIVE HAVING FLT3 INHIBITORY ACTIVITY, AND USE THEREOF

TECHNICAL FIELD

The present invention relates to a novel quinazoline derivative having fms-like tyrosine kinase 3 (FLT3) inhibitory activity, and a use thereof.

The present invention was made under the support of the Ministry of Science and ICT (2017Y) of the Republic of Korea with the project number NRF-2019M3A9A8066500, the research management institution for the project is the "National Research Foundation of Korea," the research business title is "Core Technology Development Project/Bio & Medical Technology Development Project/Research Program for New Drug Target Identification and Validation," the research project title is "Validation of JNK inhibitor having effects of suppressing nerve cell apoptosis and improving cognitive functions as therapeutic agent for Alzheimer's disease," and the research period is "Jun. 1, 2019 to Feb. 29, 2020."

The present patent application claims priority to and the benefit of Korean Patent Application No. 10-2020-0124692, filed on Sep. 25, 2020, the disclosure of which is incorporated herein by reference in its entirety.

BACKGROUND ART

As fms-like tyrosine kinase 3 (FLT3) is a type of transmembrane receptor tyrosine kinase expressed in lymph-hematopoietic cells and is a target of acute myeloid leukemia (AML), it is drawing attention because FLT3 is involved in the regulation of survival, proliferation and differentiation of hematopoietic stem/progenitor cells in an AML patient. When the FLT3 ligand binds to FLT3 kinase, FLT3 is activated and autophosphorylated. Subsequently, FLT3 activates multiple downstream signaling pathways including signal transducer and activator of transcription 5 (STATS), Ras/mitogen-activated protein kinase (Ras/MAPK) and phosphatidylinositol 3-kinase/Akt pathways, consequently playing an important role in the proliferation and survival of cells and immune responses. However, mutated FLT3 causes activation regardless of the presence or absence of a ligand. FLT3 mutations can be categorized by mutation location and type, represented by internal tandem duplications (ITDs) and point mutations in the tyrosine kinase domain (TKD). FLT3-ITD mutations account for 20 to 30% of AML patients and are importantly directly linked to an abnormal increase in leukocytes and poor prognosis, and point mutations in the TKD are found in 5% of AML cases. Despite the importance of finding a cure for AML, the number of therapeutic materials approved to date, such as midostaurin and gilteritinib (ASP2215), is very small.

Protein kinase inhibitors can be classified into type I, type II and type III based on their binding mode (Non-Patent Document 0001). Among these inhibitors, type II kinase inhibitors can acquire selectivity having additional interactions with the DFG pocket adjacent to the ATP-binding pocket on top of the hinge hydrogen bond at the ATP-site and exhibit promising efficacy (Non-Patent Document 0002).

Quinazoline structures are well-known as privileged structures in medicinal chemistry and exhibit diverse biologically active properties, but were first attempted in type II PKI modification. By introducing such a structure into an in-house type II kinase inhibitor, a novel FLT3 inhibitor could be discovered. Further, the novel FLT3 inhibitor of the present invention achieved a selectivity profile, particularly compared to cKIT and FMS kinases.

(Non-Patent Document 0001) Wu P, Nielsen T E, Clausen M H. FDA-approved small-molecule kinase inhibitors. Trends Pharmacol Sci. 2015; 36(7):422-439.

(Non-Patent Document 0002) Versele, M, Haefner, B, Wroblowski, B, Stansfield, I, Mevellec, L, Gilissen, R, et al. Covalent Flt3-Cys828 inhibition represents a novel therapeutic approach for the treatment of Flt3-ITD and Flt3-D835 mutant acute myeloid leukemia. Cancer Res. 2016; 76(14):4800.

DISCLOSURE

Technical Problem

The present invention has been made to solve the problem as described above, and as a result of intensive studies to find a novel material which is likely to be developed as a therapeutic agent for acute myeloid leukemia (AML), the present inventors identified a novel quinazoline derivative showing FLT3 inhibitory activity, thereby completing the present invention based on this.

Thus, an object of the present invention is to provide a novel quinazoline derivative having FLT3 inhibitory activity, or a pharmaceutically acceptable salt thereof.

Another object of the present invention is to provide a method for preparing a novel quinazoline derivative having FLT3 inhibitory activity.

Still another object of the present invention is to provide a pharmaceutical composition for preventing or treating an acute leukemia disease, including the imidazole derivative or a pharmaceutically acceptable salt thereof as an active ingredient.

However, technical problems to be solved by the present invention are not limited to the aforementioned problems, and other problems that are not mentioned may be clearly understood by those skilled in the art from the following description.

Technical Solution

To achieve the aforementioned objects of the present invention, the present invention provides a compound represented by the following Chemical Formula 7 or a pharmaceutically acceptable salt thereof.

[Chemical Formula 7]

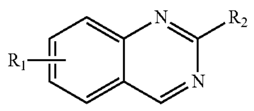

In Chemical Formula 7, $R_1$ is

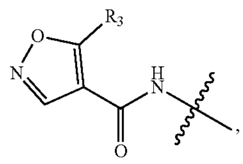
, $R_2$ is selected from the group consisting of indazolyl, naphthalenyl, dihydrobenzofuranyl, pyridinyl, acetyl piperidine, phenyl which is unsubstituted or substituted with one or more non-hydrogen substituents, pyrazolyl which is unsubstituted or substituted with one or more non-hydrogen substituents, dihydroisoxazole which is unsubstituted or substituted with one or more non-hydrogen substituents,

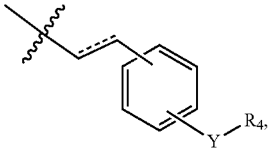

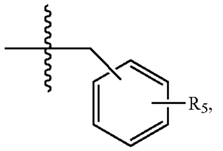

or a $C_3$-$C_7$ cycloalkyl, the non-hydrogen substituent in $R_2$ is selected from the group consisting of

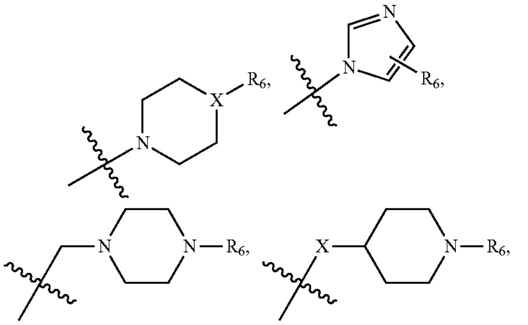

phenyl, hydroxy, a $C_1$-$C_6$ alkyl, a $C_1$-$C_6$ halogenated alkyl, or a halogen atom, $R_3$ is a hydrogen atom, hydroxy, a $C_1$-$C_6$ alkyl or a $C_1$-$C_6$ halogenated alkyl, $R_4$ is a hydrogen atom, hydroxy or a $C_1$-$C_6$ alkyl, or is absent, here, X is a nitrogen or oxygen atom, and Y is a halogen or oxygen atom, $R_5$ is a hydrogen atom, hydroxy, a halogen atom or a $C_1$-$C_6$ halogenated alkyl, $R_6$ is a hydrogen atom, hydroxy or a $C_1$-$C_6$ alkyl, and a connecting line expressed as a double line ( ------ ) of a solid line and a dotted line represents a single carbon-carbon bond or a double carbon-carbon bond.

Further, the present invention provides a pharmaceutical composition for preventing or treating acute myeloid leukemia (AML), including the derivative of Chemical Formula 7 or a pharmaceutically acceptable salt thereof as an active ingredient.

As an exemplary embodiment of the present invention, the composition may inhibit the activity of fms-like tyrosine kinase 3 (FLT 3).

In addition, the present invention provides a method for treating acute myeloid leukemia (AML), the method including: administering the derivative of Chemical Formula 7 or a pharmaceutically acceptable salt thereof to an individual.

Furthermore, the present invention provides a use of the derivative of Chemical Formula 7 or a pharmaceutically acceptable salt thereof for treating acute myeloid leukemia (AML) disease.

Advantageous Effects

Since a novel quinazoline derivative or a pharmaceutically acceptable salt thereof according to the present invention exhibits inhibitory activity as an excellent target against fms-like tyrosine kinase 3 (FLT 3), a pharmaceutical composition including the derivative can be usefully used for the prevention and treatment of cancer including acute myeloid leukemia (AML).

DESCRIPTION OF DRAWINGS

FIG. 1 is a view illustrating the selective FLT3 inhibitory activity of Compound 7d of the present invention.

MODES OF THE INVENTION

Hereinafter, the present invention will be described in detail.

The present invention provides a compound of the following Chemical Formula 7, or a pharmaceutically acceptable salt thereof.

[Chemical Formula 7]

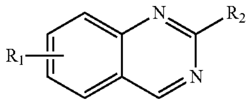

In Chemical Formula 7, $R_1$ is

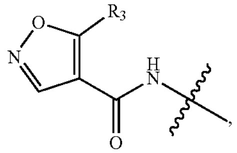

$R_2$ is selected from the group consisting of indazolyl, naphthalenyl, dihydrobenzofuranyl, pyridinyl, acetyl piperidine, phenyl which is unsubstituted or substituted with one or more non-hydrogen substituents, pyrazolyl which is unsubstituted or substituted with one or more non-hydrogen substituents, dihydroisoxazole which is unsubstituted or substituted with one or more non-hydrogen substituents,

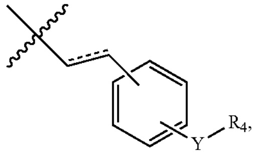

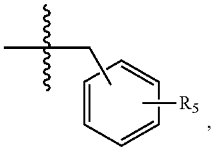

or a $C_3$-$C_7$ cycloalkyl, the non-hydrogen substituent in $R_2$ is selected from the group consisting of

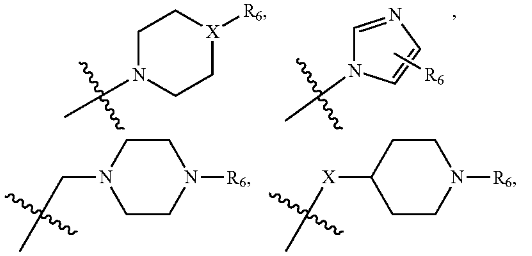

phenyl, hydroxy, a $C_1$-$C_6$ alkyl, a $C_1$-$C_6$ halogenated alkyl, or a halogen atom, $R_3$ is a hydrogen atom, hydroxy, a $C_1$-$C_6$ alkyl or a $C_1$-$C_6$ halogenated alkyl, $R_4$ is a hydrogen atom, hydroxy or a $C_1$-$C_6$ alkyl, or is absent, here, X is a nitrogen or oxygen atom, and Y is a halogen or oxygen atom, $R_5$ is a hydrogen atom, hydroxy, a halogen atom or a $C_1$-$C_6$ halogenated alkyl, $R_6$ is a hydrogen atom, hydroxy or a $C_1$-$C_6$ alkyl, and a connecting line expressed as a double line (═══) of a solid line and a dotted line represents a single carbon-carbon bond or a double carbon-carbon bond.

Here, "alkyl" refers to a straight or branched saturated hydrocarbon group generally having a specified number of carbon atoms (for example, 1 to 12 carbon atoms). Examples of an alkyl group include methyl, ethyl, n-propyl, isopropyl, n-butyl, sec-butyl, isobutyl, tert-butyl, n-pentyl, n-hexyl, n-heptyl, and the like without limitation. An alkyl may be attached to a parent group or substrate at any ring atom provided that the attachment does not violate valence requirements. Similarly, an alkyl group or an alkenyl group may include one or more non-hydrogen substituents provided that the attachment does not violate valence requirements.

"Cycle" refers to a saturated monocyclic and polycyclic hydrocarbon ring generally having a specified number of carbon atoms, including a ring (that is, a $C_{3-10}$ cycloalkyl refers to a cycle having 3, 4, 5, 6, 7, 8, 9 or 10 carbon atoms as a ring member).

"Halogen" is an element belonging to Group 17 of the Periodic Table, and easily becomes an anion by obtaining electrons from other elements because there are seven electrons in the outermost electron shell. The halogen is usually present in the form of other elements and compounds because it is the most non-metallic and highly reactive in each period. Examples thereof include fluorine, chlorine, bromine, iodine, and the like.

"Alkyl halide" refers to a compound in which one hydrogen atom of an alkyl is substituted with a halogen element, and is named a primary, secondary, tertiary alkyl halide, and the like, according to the number of carbons attached to the carbon attached to the halogen. Examples of the alkyl halide include methyl halide, vinyl halide, aryl halide, allyl halide, benzyl halide, and the like without limitation. The alkyl halide may be attached to a parent group or a substrate at any ring atom if the attachment does not violate valence requirements.

"Hydroxy" is a functional group whose structural formula is represented by —OH.

In an exemplary embodiment of the present invention, the compound of Chemical Formula 7 may have a structure of the following Chemical Formula 7'.

[Chemical Formula 7']

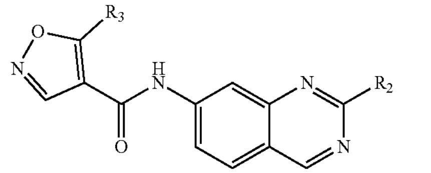

In Chemical Formula 7', $R_2$ is selected from the group consisting of indazolyl, naphthalenyl, dihydrobenzofuranyl, pyridinyl, acetyl piperidine, phenyl which is unsubstituted or substituted with one or more non-hydrogen substituents, pyrazolyl which is unsubstituted or substituted with one or more non-hydrogen substituents, dihydroisoxazole which is unsubstituted or substituted with one or more non-hydrogen substituents,

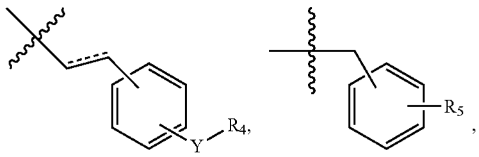

or a $C_3$-$C_7$ cycloalkyl, the non-hydrogen substituent in $R_2$ is selected from the group consisting of

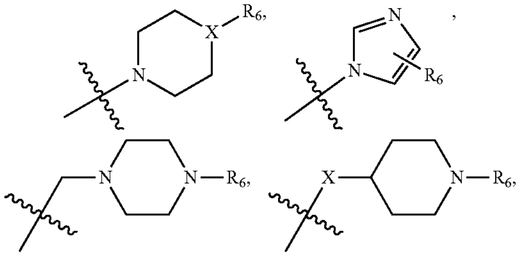

phenyl, hydroxy, a $C_1$-$C_6$ alkyl, a $C_1$-$C_6$ halogenated alkyl, or a halogen atom, $R_3$ is a hydrogen atom, hydroxy, a $C_1$-$C_6$ alkyl or a $C_1$-$C_6$ halogenated alkyl, $R_4$ is a hydrogen atom, hydroxy or a $C_1$-$C_6$ alkyl, or is absent, here, X is a nitrogen or oxygen atom, and Y is a halogen or oxygen atom, $R_5$ is a hydrogen atom, hydroxy, a halogen atom or a $C_1$-$C_6$ halogenated alkyl, $R_6$ is a hydrogen atom, hydroxy or a $C_1$-$C_6$ alkyl, and A connecting line expressed as a double line (═══) of a solid line and a dotted line represents a single carbon-carbon bond or a double carbon-carbon bond.

As another exemplary embodiment of the present invention, in the chemical formulae, $R_2$ is selected from the group consisting of indazolyl, pyridinyl, phenyl which is unsubstituted or substituted with one or more non-hydrogen substituents, or

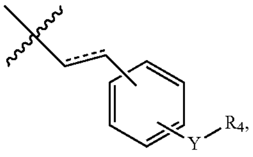

the non-hydrogen substituent in $R_2$ is selected from the group consisting of

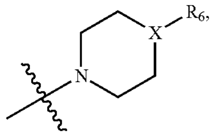 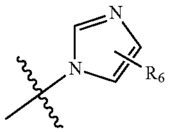 ,

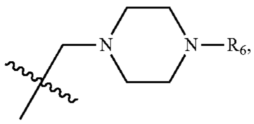 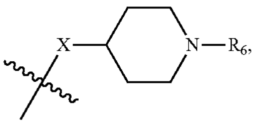

or a $C_1$-$C_6$ halogenated alkyl, $R_3$ is a $C_1$-$C_6$ alkyl, $R_4$ is a $C_1$-$C_6$ alkyl, here, X is an oxygen atom, Y is a halogen or oxygen atom, and $R_6$ is hydrogen or a $C_1$-$C_6$ alkyl, A connecting line expressed as a double line ( ------ ) of a solid line and a dotted line represents a single carbon-carbon bond or a double carbon-carbon bond.

As still another exemplary embodiment of the present invention, in the chemical formulae, $R_3$ may be a $C_1$-$C_6$ alkyl.

As yet another exemplary embodiment of the present invention, in the chemical formulae, $R_2$ may be

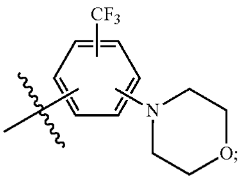 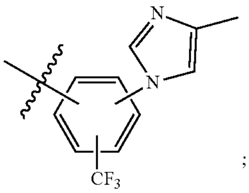 ;

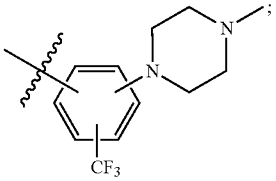

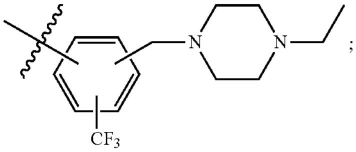 ; 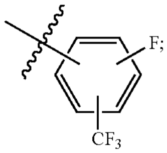

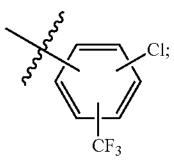 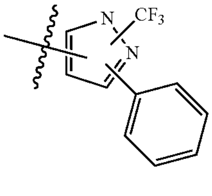 ;

-continued

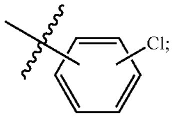 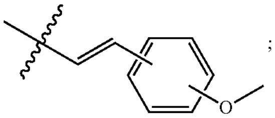 ;

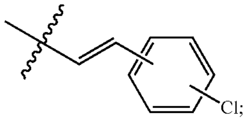 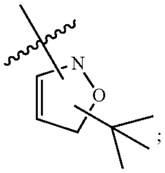

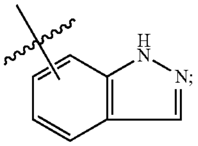 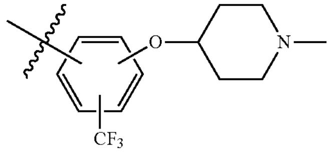 ;

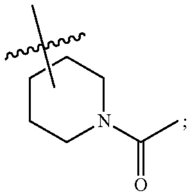 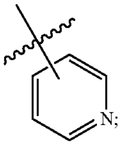 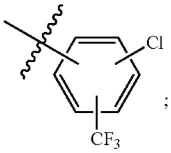 ;

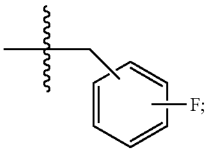 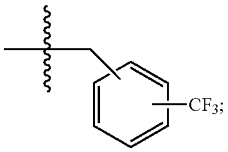

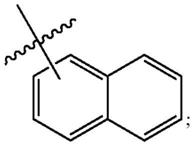 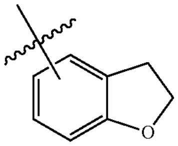 or

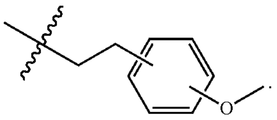

As yet another exemplary embodiment of the present invention, in the chemical formulae, $R_3$ is a $C_1$-$C_6$ alkyl, and $R_2$ may be

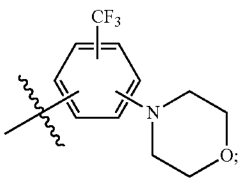 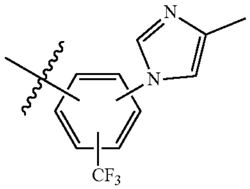 ;

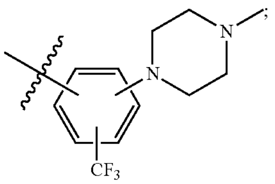

-continued

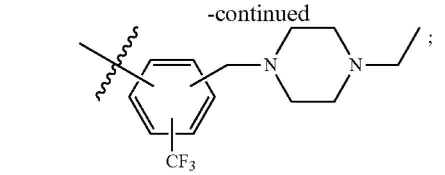

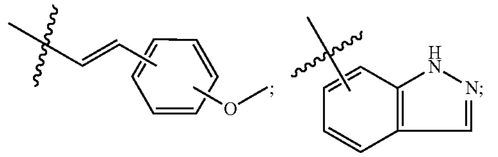

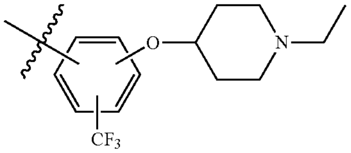

or

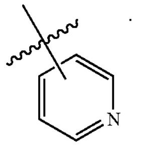

.

As yet another exemplary embodiment of the present invention, the quinazoline compound of Chemical Formula 7 may be 5-methyl-N-(2-(3-morpholino-5-(triflurومethyl)phenyl)quinazolin-7-yl)isoxazole-4-carboxamide (7a);

5-methyl-N-(2-(3-morpholino-5-(trifluoromethyl)phenyl)quinazolin-7-yl)isoxazole-4-carboxamide (7b);

5-methyl-N-(2-(3-(4-methyl-1H-imidazol-1-yl)-5-(trifluoromethyl)phenyl)quinazolin-7-yl)isoxazole-4-carboxamide (7c);

5-methyl-N-(2-(3-(4-methylpiperazin-1-yl)-5-(trifluoromethyl)phenyl)quinazolin-7-yl)isoxazole-4-carboxamide (7d);

N-(2-(3-((4-ethylpiperazin-1-yl)methyl)-5-(trifluoromethyl)phenyl)quinazolin-7-yl)-5-methylisoxazole-4-carboxamide (7e);

N-(2-(3-fluoro-5-(trifluoromethyl)phenyl)quinazolin-7-yl)-5-methylisoxazole-4-carboxamide (7f);

N-(2-(4-chloro-3-(trifluoromethyl)phenyl)quinazolin-7-yl)-5-methylisoxazole-4-carboxamide (7g);

5-methyl-N-(2-(1-phenyl-5-(trifluoromethyl)-1H-pyrazol-4-yl)quinazolin-7-yl)isoxazole-4-carboxamide (7h);

N-(2-(3-chlorophenyl)quinazolin-7-yl)-5-methylisoxazole-4-carboxamide (7i);

(E)-N-(2-(4-methoxystyryl)quinazolin-7-yl)-5-methylisoxazole-4-carboxamide (7j);

(E)-N-(2-(4-chlorostyryl)quinazolin-7-yl)-5-methylisoxazole-4-carboxamide (7k);

N-(2-(5-(tert-butyl)isoxazol-3-yl)quinazolin-7-yl)-5-methylisoxazole-4-carboxamide (7l);

N-(2-(1H-indazol-5-yl)quinazolin-7-yl)-5-methylisoxazole-4-carboxamide (7m);

5-methyl-N-(2-(3-((1-methylpiperidin-4-yl)oxy)-5-(trifluoromethyl)phenyl)quinazolin-7-yl)isoxazole-4-carboxamide (7n);

N-(2-(1-acetylpiperidin-4-yl)quinazolin-7-yl)-5-methylisoxazole-4-carboxamide (7o);

5-methyl-N-(2-(pyridin-4-yl)quinazolin-7-yl)isoxazole-4-carboxamide (7p);

5-methyl-N-(2-(pyridin-2-yl)quinazolin-7-yl)isoxazole-4-carboxamide (7q);

N-(2-(3,4-dichlorophenyl)quinazolin-7-yl)-5-methylisoxazole-4-carboxamide (7r);

N-(2-(4-fluorobenzyl)quinazolin-7-yl)-5-methylisoxazole-4-carboxamide (7s);

5-methyl-N-(2-(2-(trifluoromethyl)benzyl)quinazolin-7-yl)isoxazole-4-carboxamide (7t);

5-methyl-N-(2-(naphthalen-2-yl)quinazolin-7-yl)isoxazole-4-carboxamide (7u);

N-(2-(2,3-dihydrobenzofuran-5-yl)quinazol in-7-yl)-5-methylisoxazole-4-carboxamide (7v); or N-(2-(4-methoxyphenethyl)quinazolin-7-yl)-5-methylisoxazole-4-carboxamide (7w).

The present invention provides a pharmaceutical composition for preventing or treating cancer, including the derivative of Chemical Formula 7 or a pharmaceutically acceptable salt thereof as an active ingredient.

As yet another exemplary embodiment of the present invention, the cancer disease may be acute myeloid leukemia (AML).

As yet another exemplary embodiment of the present invention, the composition may inhibit the activity of fms-like tyrosine kinase 3 (FLT 3).

Further, for the compound in the present invention, as shown in the following Reaction Scheme 1, the quinazoline derivative of claim 1 may be prepared by a method including: synthesizing a compound of Chemical Formula 2 by forming an amide in a compound of Chemical Formula 1, and then reducing the amide group in the compound of Chemical Formula 2 to a compound of Chemical Formula 3 using borane (Steps 1 and 2);

preparing the compounds of Chemical Formulae 4a-l and 4n-u by forming an amide in the compound of Chemical Formula 3 prepared in Steps 1 and 2 with various benzoyl chlorides (Step 3);

obtaining a dihydro quinazoline compound by irradiating the compounds of Chemical Formulae 4a-l and 4n-u prepared in Step 3 with microwaves for cyclization, and then preparing compounds of Chemical Formulae 5a-l and 5n-u, which are quinazoline derivatives that are core intermediates by treating the dihydro quinazoline compound with a p-chloranil oxidant without further purification (Step 4);

preparing compounds of Chemical Formula 6a-v by reducing the nitro groups in the compounds of Chemical Formulae 5a-l and 5n-u to aniline using an Fe catalyst (Step 5);

preparing Compounds 7a-v represented by [Chemical Formula 1] which are final compounds by forming an amide in the compounds of Chemical Formula 6a-v with isoxazole chloride (Step 6); and preparing Compound 7w by subjecting Compound 7j to a reduction process by hydrogenation (Step 7), and the method is not limited thereto.

[Reaction Scheme 1]

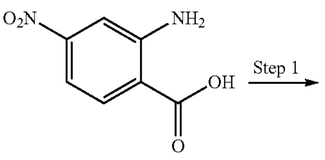

1

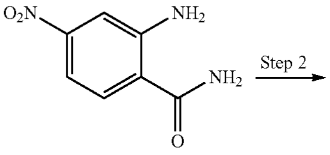

2

-continued

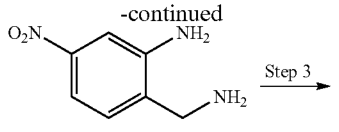

3

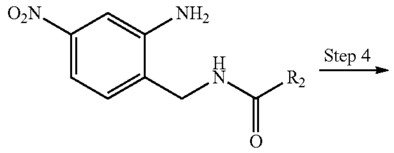

4a-l, 4n-u

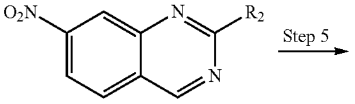

5a-l, 5n-u

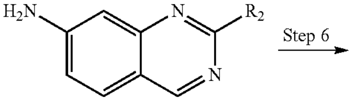

6a-v

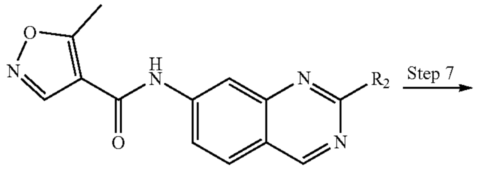

7a-v

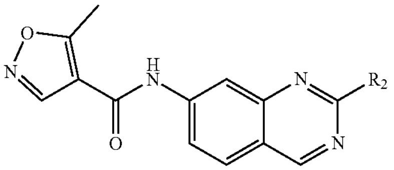

7w

In addition, for the compound in the present invention, as shown in the following Reaction Scheme 2, the quinazoline derivative of claim 1 may be prepared by a method including: synthesizing a compound of Chemical Formula 2 by forming an amide in a compound of Chemical Formula 1, and then reducing the amide group in the compound of Chemical Formula 2 to a compound of Chemical Formula 3 using borane (Steps 1 and 2);

first synthesizing tetrahydro quinazoline using indazole-6-carbaldehyde in the compound of Chemical Formula 3 prepared in Steps 1 and 2 (Step 3-1);

thereafter, preparing Compounds 7m and 7v represented by [Chemical Formula 1] which are final compounds by subjecting the tetrahydro quinazoline to steps which are the same as in Reaction Scheme 1 (Steps 5 and 6), and the method is not limited to this example.

[Reaction Scheme 2]

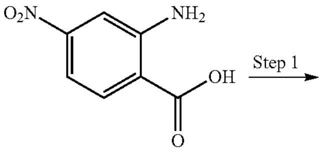

1

-continued

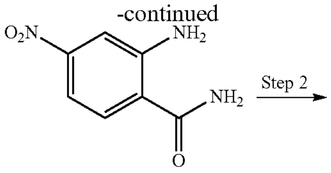

2

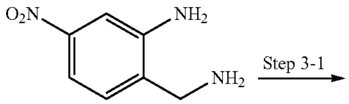

3

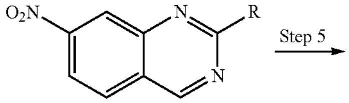

5m, 5v

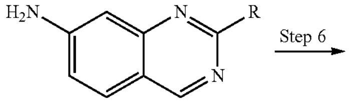

6m, 6v

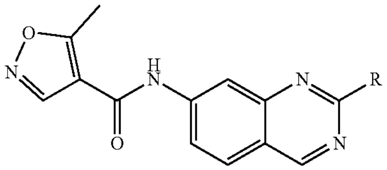

7m, 7v

Meanwhile, the compound of the present invention may be used in the form of a pharmaceutically acceptable salt, and as the salt, an acid addition salt formed by a pharmaceutically acceptable free acid is useful.

As the term "salt" used herein, an acid addition salt formed by a pharmaceutically acceptable free acid is useful. The acid addition salt is obtained from inorganic acids such as hydrochloric acid, nitric acid, phosphoric acid, sulfuric acid, hydrobromic acid, hydroiodic acid, nitrous acid or phosphorous acid, and nontoxic organic acids such as aliphatic mono- and dicarboxylates, phenyl-substituted alkanoates, hydroxyalkanoates and alkanedioates, aromatic acids, aliphatic and aromatic sulfonic acids. Such pharmaceutically nontoxic salts include sulfates, pyrosulfates, bisulfates, sulfites, bisulfites, nitrates, phosphates, monohydrogen phosphates, dihydrogen phosphates, metaphosphates, pyrophosphates, chlorides, bromides, iodides, fluorides, acetates, propionates, decanoates, caprylates, acrylates, formates, isobutyrates, caprates, heptanoates, propiolates, oxalates, malonates, succinates, suberates, sebacates, fumarates, maleates, butene-1,4-dioates, hexane-1,6-dioates, benzoates, chlorobenzoates, methyl benzoates, dinitrobenzoates, hydroxybenzoates, methoxybenzoates, phthalates, terephthalates, benzenesulfonates, toluenesulfonates, chlorobenzenesulfonates, xylenesulfonates, phenyl acetates, phenyl propionates, phenyl butyrates, citrates, lactates, β-hydroxybutyrates, glycolates, malates, tartrates, m ethane sulfonates, propane sulfonates, naphthalene-1-sulfonates, naphthalene-2-sulfonates or mandelates.

The acid addition salt according to the present invention may be prepared by typical methods, for example, dissolving the compound in an excess aqueous acid solution, and precipitating the salt using a water-miscible organic solvent, for example, methanol, ethanol, acetone or acetonitrile.

Further, the acid addition salt may also be prepared by evaporating the solvent or excess acid from this mixture, and then drying the mixture or suction-filtering a precipitated salt.

In addition, a pharmaceutically acceptable metal salt may be prepared using a base. An alkali metal or alkaline earth metal salt is obtained by, for example, dissolving the compound in an excess alkali metal hydroxide or alkaline-earth metal hydroxide solution, filtering the non-soluble compound salt, evaporating the filtrate, and drying the result product. In this case, preparing a sodium, potassium or calcium salt as the metal salt is pharmaceutically suitable. A silver salt corresponding to this is obtained by reacting the alkali metal or alkaline earth metal salt with a suitable silver salt (for example, silver nitrate).

Further, the compound of the present invention includes not only pharmaceutically acceptable salts, but also all salts, isomers, hydrates and solvates which can be prepared by typical methods.

As can be confirmed in the following Examples, the compound of Chemical Formula 7 may be used as a FLT3 inhibitor, and as described in the Background Art of the invention, it is well known to those skilled in the art that the FLT3 inhibitor can be used for cancer treatment.

The present invention provides a pharmaceutical composition for preventing or treating cancer, including the quinazoline derivative of Chemical Formula 7 or a pharmaceutically acceptable salt thereof as an active ingredient, and more specifically, a pharmaceutical composition for preventing or treating acute myeloid leukemia (AML), a use of the quinazoline derivative of Chemical Formula 7 or a pharmaceutically acceptable salt thereof for treating the disease, and a method for treating the disease, the method including: administering a therapeutically effective amount of the compound of Chemical Formula 7 or a pharmaceutically acceptable salt thereof to a subject.

As used herein, the term "prevention" refers to all actions that suppress acute myeloid leukemia (AML) or delay the onset of acute myeloid leukemia (AML) by administering the pharmaceutical composition according to the present invention.

As used herein, the term "treatment" refers to all actions that ameliorate or beneficially change the symptoms of acute myeloid leukemia (AML) by administering the pharmaceutical composition according to the present invention.

The pharmaceutical composition of the present invention may include a pharmaceutically acceptable carrier in addition to an active ingredient. In this case, the pharmaceutically acceptable carrier is typically used during formulation, and includes lactose, dextrose, sucrose, sorbitol, mannitol, starch, gum acacia, calcium phosphate, alginate, gelatin, calcium silicate, microcrystalline cellulose, polyvinylpyrrolidinone, cellulose, water, syrup, methylcellulose, methyl hydroxybenzoate, propyl hydroxybenzoate, talc, magnesium stearate, mineral oil, and the like, but is not limited thereto. Furthermore, the pharmaceutically acceptable carrier may further include a lubricant, a wetting agent, a sweetening agent, a flavoring agent, an emulsifier a suspending agent, a preservative, and the like in addition to the above ingredients.

The pharmaceutical composition of the present invention may be orally administered or may be parenterally administered (for example, intravenously, subcutaneously, intraperitoneally, or topically applied), and the dosage may vary depending on a patient's condition and body weight, severity of disease, drug form, and administration route and period according to the desired method, but the dosage may be properly selected by the person skilled in the art.

The pharmaceutical composition of the present invention is administered in a pharmaceutically effective amount. As used herein, the "pharmaceutically effective amount" refers to an amount sufficient to treat diseases at a reasonable benefit/risk ratio applicable to medical treatment, and an effective dosage level may be determined according to factors including the type of a patient's disease, the severity of disease, the activity of drugs, sensitivity to drugs, administration time, administration route, excretion rate, treatment period, and simultaneously used drugs, and other factors well known in the medical field. The pharmaceutical composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this amount may be easily determined by those skilled in the art.

Specifically, an effective amount of the pharmaceutical composition of the present invention may vary depending on the age, gender, condition, and body weight of a patient, the absorption of the active ingredient in the body, inactivation rate and excretion rate, disease type, and the drugs used in combination, and in general, 0.0001 to 1000 mg, preferably 0.001 to 500 mg of the pharmaceutical composition of the present invention per 1 kg of body weight may be administered daily or every other day or may be dividedly administered once to three times a day. However, since the effective amount may be increased or decreased depending on the administration route, the severity of obesity, gender, body weight, age, and the like, the dosage is not intended to limit the scope of the present invention in any way.

In the present invention, "an individual" refers to a subject in need of treatment of a disease, and more specifically, refers to a mammal such as a human or a non-human primate, a mouse, a dog, a cat, a horse, and a cow.

Hereinafter, preferred preparation examples for helping the understanding of the present invention will be suggested. However, the following examples are provided only to more easily understand the present invention, and the contents of the present invention are not limited by the following preparation examples.

<Preparation Example 1> Synthesis of 2-amino-4-nitrobenzamide (2)

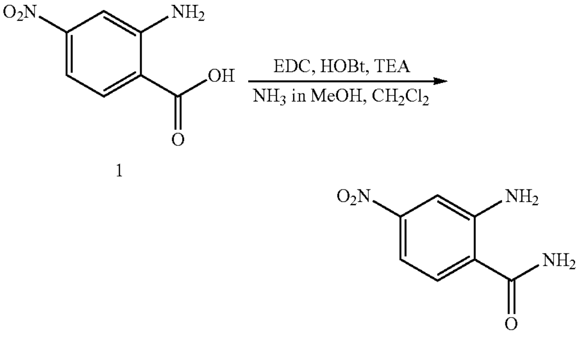

1

2

EDC (690.12 mg, 3.6 mmol), HOBt (450.42 mg, 3 mmol), TEA (0.72 ml) and $NH_3$ in MeOH (2 M, 40 ml) were added to a mixture of 2-amino-4-nitro-benzoic acid (546.39 mg, 3 mmol) and $CH_2Cl_2$ (30 ml), and the resulting mixture was stirred at room temperature overnight. After the reaction was confirmed, the resulting precipitate was filtered under vacuum to obtain 2-amino-4-nitro-benzamide (2) (487.8 mg, 89.76%).

<Preparation Example 2> Synthesis of 2-(aminomethyl)-5-nitroaniline (3)

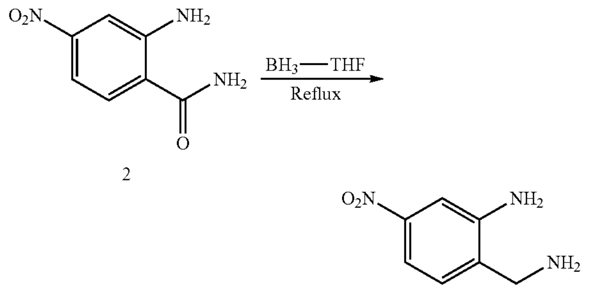

2

3

A borane-tetrahydrofuran complex (1.0 M solution of tetrahydrofuran) (2.2 ml) was added to a solution of 2-amino-4-nitrobenzamide (100.0 mg) in tetrahydrofuran (6.0 ml), and the resulting mixture was stirred for 2 hours. After the reaction was completed, the mixture was cooled. Subsequently, methanol was added to the mixture, the mixture was neutralized with methanol containing 10% hydrogen chloride, and then the solvent was concentrated under reduced pressure. Thereafter, a 1 N sodium hydroxide solution was added to the residue to perform extraction with methylene chloride. The organic layer was washed with saturated brine and dried over anhydrous sodium sulfate. After the solvent was concentrated under reduced pressure, Compound 3 (87.47 mg, 95.13%) was obtained; $^1H$ NMR (400 MHz, DMSO-$d_6$) δ 7.28-7.22 (m, 1H), 6.48 (s, 2H), 5.73 (dd, J=7.6, 1.9 Hz, 2H), 5.27 (s, 2H).

<Preparation Example 3> General Procedure A: Synthesis of Compounds 4a-l and 4n-u

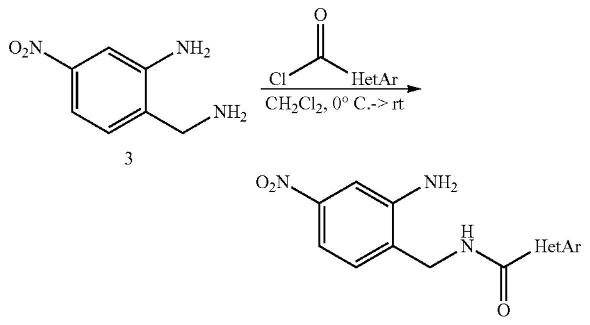

3

4

2-Amino-4-nitrobenzylamine (1 eq) and triethylamine (TEA) (3.5 eq) were stirred in dichloromethane (DCM) (0.1 M) while maintaining the temperature at 0° C., DCM (0.1 M) containing benzoyl chloride (0.9 eq) was slowly added dropwise thereto, and the temperature was continuously maintained at 0° C. Thereafter, the mixture was stirred at room temperature for about 3 hours, water was added to the mixed solvent, and an organic layer was obtained by adding water to the mixed solvent to separate the layers. The remaining water was removed using anhydrous $Na_2SO_4$, the residue was filtered, and then silica gel column chromatography was performed to obtain Compound 4.

The following compounds were obtained by the method of Preparation Example 3.

N-(2-amino-4-nitrobenzyl)-4-morpholino-3-(trifluoromethyl)benzamide (4a)

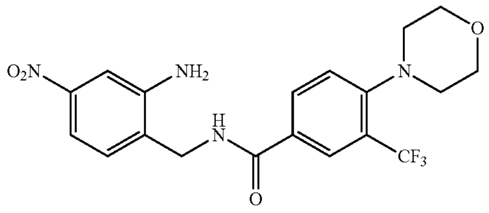 [SMILES: Nc1cc([N+](=O)[O-])ccc1CNC(=O)c1ccc(N2CCOCC2)c(C(F)(F)F)c1]

The compound was synthesized from Compound 3 using General Procedure A. The compound was purified by column chromatography (EA:Hex=1:1) to obtain a target Compound 4a (91%) as a solid; HRMS (ESI$^+$) calculated for $C_{19}H_{19}F_3N_4O_4$ $[M+H]^+$: 425.1358, found 425.0768.

N-(2-amino-4-nitrobenzyl)-3-morpholino-5-(trifluoromethyl)benzamide (4b)

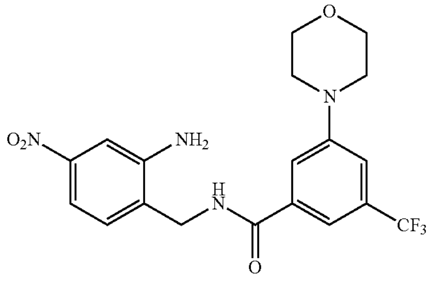 [SMILES: Nc1cc([N+](=O)[O-])ccc1CNC(=O)c1cc(N2CCOCC2)cc(C(F)(F)F)c1]

The compound was synthesized from Compound 3 using General Procedure A. A target Compound 4b (70%) was obtained as a solid; HRMS (ESI$^+$) calculated for $C_{19}H_{19}F_3N_4O_4$ $[M+H]^+$: 425.1358, found 425.3289.

N-(2-amino-3-nitrophenyl)-3-(4-methyl-1H-imidazol-1-yl)-5 (trifluoromethyl)benzamide (4c)

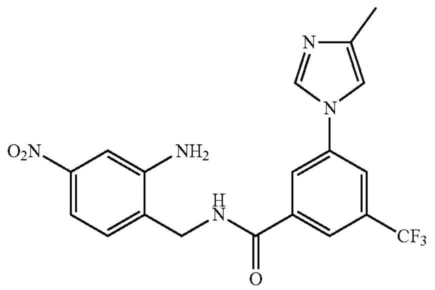 [SMILES: Cc1cn(-c2cc(C(=O)NCc3ccc([N+](=O)[O-])cc3N)cc(C(F)(F)F)c2)cn1]

The compound was synthesized from Compound 3 using General Procedure A. A target Compound 4c (57.2%) was obtained as a solid; $^1$H NMR (400 MHz, DMSO-$d_6$) δ 9.34 (t, J=5.8 Hz, 1H), 8.38 (s, 1H), 8.36 (d, J=1.3 Hz, 1H), 8.22 (s, 1H), 8.13 (s, 1H), 7.67 (s, 1H), 7.52 (d, J=2.4 Hz, 1H), 7.37 (dd, J=8.3, 2.4 Hz, 1H), 7.28 (d, J=8.4 Hz, 1H), 5.82 (s, 2H), 4.44 (d, J=5.8 Hz, 2H), 2.18 (d, J=0.8 Hz, 3H); HRMS (ESI$^+$) calculated for $C_{19}H_{16}F_3N_5O_3$ [M+H]$^+$: 420.1205, found 420.3815.

N-(2-amino-4-nitrobenzyl)-3-(4-methylpiperazin-1-yl)-5-(trifluoromethyl)benzamide (4d)

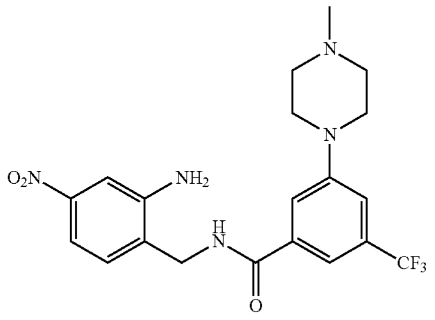 [SMILES: CN1CCN(c2cc(C(=O)NCc3ccc([N+](=O)[O-])cc3N)cc(C(F)(F)F)c2)CC1]

The compound was synthesized from Compound 3 using General Procedure A. A target Compound 4d (79%) was obtained as a solid; $^1$H NMR (400 MHz, DMSO-$d_6$) δ 9.19 (t, J=5.9 Hz, 1H), 7.68 (s, 1H), 7.57 (s, 1H), 7.50 (d, J=2.4 Hz, 1H), 7.36 (dd, J=8.3, 2.5 Hz, 2H), 7.23 (d, J=8.3 Hz, 1H), 5.82 (s, 2H), 4.39 (d, J=5.8 Hz, 2H), 3.31-3.27 (m, 4H), 2.48-2.44 (m, 4H), 2.23 (s, 3H); HRMS (ESI$^+$) calculated for $C_{20}H_{22}F_3N_5O_3$ [M+H]$^+$: 438.1675, found 438.3749.

N-(2-amino-4-nitrobenzyl)-3-((4-ethylpiperazin-1-yl)methyl)-5-(trifluoromethyl)benzamide (4e)

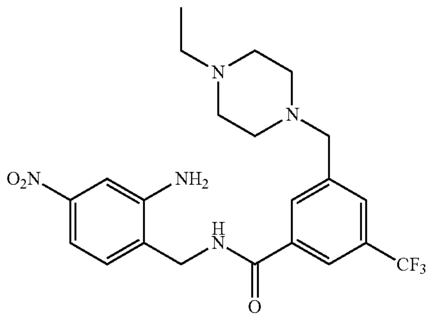 [SMILES: CCN1CCN(Cc2cc(C(=O)NCc3ccc([N+](=O)[O-])cc3N)cc(C(F)(F)F)c2)CC1]

The compound was synthesized from Compound 3 using General Procedure A. A target Compound 4e (67%) was obtained as a solid; $^1$H NMR (400 MHz, DMSO-$d_6$) δ 9.31 (t, J=5.8 Hz, 1H), 8.15 (d, J=5.3 Hz, 2H), 7.85 (s, 1H), 7.52 (d, J=2.4 Hz, 1H), 7.38 (dd, J=8.3, 2.4 Hz, 1H), 7.26 (d, J=8.3 Hz, 1H), 5.84 (s, 2H), 4.42 (d, J=5.8 Hz, 2H), 3.64 (s, 2H), 3.40-3.33 (s, 2H), 3.33-3.29 (m, 4H), 2.45 (s, 4H), 1.02 (t, J=6.9 Hz, 3H); HRMS (ESI$^+$) calculated for $C_{22}H_{26}F_3N_5O_3$ [M+H]$^+$: 466.1988, found 466.5619.

N-(2-amino-4-nitrobenzyl)-3-fluoro-5-(trifluoromethyl)benzamide (4f)

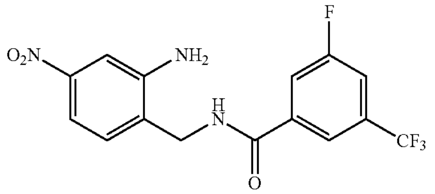 [SMILES: Nc1cc([N+](=O)[O-])ccc1CNC(=O)c1cc(F)cc(C(F)(F)F)c1]

The compound was synthesized from Compound 3 using General Procedure A. A target Compound 4f (65%) was obtained as a solid; $^1$H NMR (400 MHz, DMSO-$d_6$) δ 9.35 (t, J=5.8 Hz, 1H), 8.12 (d, J=0.6 Hz, 1H), 8.04 (d, J=9.2 Hz, 1H), 7.95 (d, J=8.5 Hz, 1H), 7.51 (d, J=2.4 Hz, 1H), 7.36 (dd, J=8.3, 2.4 Hz, 1H), 7.25 (d, J=8.4 Hz, 1H), 5.80 (s, 2H), 4.41 (d, J=5.8 Hz, 2H); HRMS (ESI$^+$) calculated for $C_{15}H_{11}F_4N_3O_3$ [M+H]$^+$: 358.0737, found 358.0891.

N-(2-amino-4-nitrobenzyl)-3-chloro-4-(trifluoromethyl)benzamide (4g)

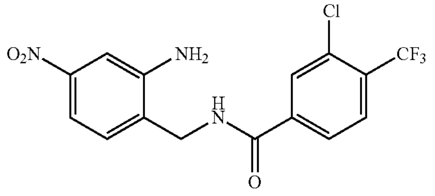 [SMILES: Nc1cc([N+](=O)[O-])ccc1CNC(=O)c1ccc(C(F)(F)F)c(Cl)c1]

The compound was synthesized from Compound 3 using General Procedure A. A target Compound 4g (73%) was obtained as a solid; $^1$H NMR (400 MHz, DMSO-$d_6$) δ 9.35

(t, J=5.8 Hz, 1H), 8.34 (d, J=2.0 Hz, 1H), 8.20 (dd, J=8.4, 2.0 Hz, 1H), 7.90 (d, J=8.4 Hz, 1H), 7.50 (d, J=2.4 Hz, 1H), 7.35 (dd, J=8.3, 2.4 Hz, 1H), 7.24 (d, J=8.4 Hz, 1H), 5.80 (s, 2H), 4.40 (d, J=5.8 Hz, 2H); HRMS ($ESI^+$) calculated for $C_{15}H_{11}ClF_3N_3O_3$ $[M+H]^+$: 374.0441, found 374.4039.

N-(2-amino-4-nitrobenzyl)-1-phenyl-5-(trifluoromethyl)-1H-pyrazole-4-carboxamide (4h)

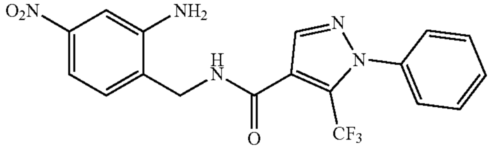 [SMILES: Nc1cc([N+](=O)[O-])ccc1CNC(=O)c1cnn(-c2ccccc2)c1C(F)(F)F]

The compound was synthesized from Compound 3 using General Procedure A. A target Compound 4h (73%) was obtained as a solid; $^1$H NMR (400 MHz, DMSO-$d_6$) δ 9.12 (t, J=6.0 Hz, 1H), 8.26-8.20 (m, 1H), 7.62-7.56 (m, 3H), 7.52 (dd, J=6.2, 2.4 Hz, 3H), 7.37 (dd, J=8.3, 2.4 Hz, 1H), 7.26 (d, J=8.4 Hz, 1H), 5.80 (s, 2H), 4.36 (d, J=6.0 Hz, 2H); HRMS ($ESI^+$) calculated for $C_{18}H_{14}F_3N_5O_3$ $[M+H]^+$: 406.1049, found 406.1158.

N-(2-amino-4-nitrobenzyl)-3-chlorobenzamide (4i)

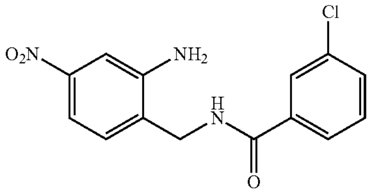 [SMILES: Nc1cc([N+](=O)[O-])ccc1CNC(=O)c1cccc(Cl)c1]

The compound was synthesized from Compound 3 using General Procedure A. A target Compound 4i (78%) was obtained as a solid; $^1$H NMR (400 MHz, DMSO-$d_6$) δ 9.16 (t, J=5.9 Hz, 1H), 7.94 (t, J=1.8 Hz, 1H), 7.89-7.84 (m, 1H), 7.64 (ddd, J=8.0, 2.1, 1.1 Hz, 1H), 7.54 (t, J=7.9 Hz, 1H), 7.50 (d, J=2.4 Hz, 1H), 7.36 (dd, J=8.3, 2.4 Hz, 1H), 7.23 (d, J=8.3 Hz, 1H), 5.81 (s, 2H), 4.37 (d, J=5.9 Hz, 2H); HRMS ($ESI^+$) calculated for $C_{14}H_{12}ClN_3O_3$ $[M+H]^+$: 306.0567, found 306.2976.

(E)-N-(2-amino-4-nitrobenzyl)-3-(4-methoxyphenyl) acrylamide (4j)

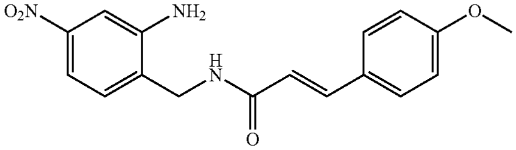 [SMILES: COc1ccc(/C=C/C(=O)NCc2ccc([N+](=O)[O-])cc2N)cc1]

The compound was synthesized from Compound 3 using General Procedure A. A target Compound 4j (79%) was obtained as a solid; $^1$H NMR (400 MHz, DMSO-$d_6$) δ 8.58 (s, 1H), 7.58-7.53 (m, 2H), 7.50 (d, J=2.4 Hz, 1H), 7.47 (d, J=15.8 Hz, 1H), 7.37 (dd, J=8.3, 2.4 Hz, 1H), 7.23 (d, J=8.3 Hz, 1H), 7.02-6.98 (m, 2H), 6.56 (d, J=15.8 Hz, 1H), 5.85 (s, 2H), 4.32 (d, J=6.1 Hz, 2H), 3.81 (s, 3H); HRMS ($ESI^+$) calculated for $C_{17}H_{17}N_3O_4$ $[M+H]^+$: 328.1219, found 328.3400.

(E)-N-(2-amino-4-nitrobenzyl)-3-(4-chlorophenyl) acrylamide (4k)

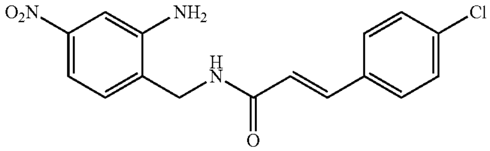 [SMILES: Nc1cc([N+](=O)[O-])ccc1CNC(=O)/C=C/c1ccc(Cl)cc1]

The compound was synthesized from Compound 3 using General Procedure A. A target Compound 4k (44%) was obtained as a solid; $^1$H NMR (400 MHz, DMSO-$d_6$) δ 8.67 (t, J=6.2 Hz, 1H), 7.65-7.58 (m, 2H), 7.53-7.43 (m, 4H), 7.35 (dd, J=8.3, 2.4 Hz, 1H), 7.22 (d, J=8.3 Hz, 1H), 6.70 (d, J=15.8 Hz, 1H), 5.82 (s, 2H), 4.31 (d, J=6.1 Hz, 2H); HRMS ($ESI^+$) calculated for $C_{16}H_{14}ClN_3O_3$ $[M+H]^+$: 332.0724, found 332.2657.

N-(2-amino-4-nitrobenzyl)-5-(tert-butyl)isoxazole-3-carboxamide (4l)

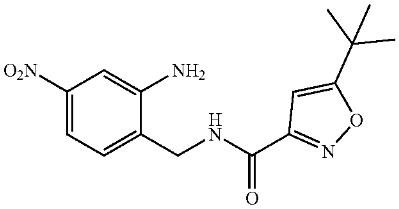 [SMILES: CC(C)(C)c1cc(C(=O)NCc2ccc([N+](=O)[O-])cc2N)no1]

The compound was synthesized from Compound 3 using General Procedure A. A target Compound 4l (37%) was obtained as a solid; $^1$H NMR (400 MHz, $CDCl_3$) δ 7.79 (s, 1H), 7.70 (dd, J=8.2, 1.7 Hz, 1H), 7.47 (s, 1H), 7.38 (d, J=8.3 Hz, 1H), 6.44 (s, 1H), 4.69 (d, J=6.5 Hz, 2H), 1.38 (s, 9H); HRMS ($ESI^+$) calculated for $C_{15}H_{18}N_4O_4$ $[M+H]^+$: 319.1328, found 319.4438.

N-(2-amino-4-nitrobenzyl)-3-((1-methylpiperidin-4-yl)oxy)-5-(trifluoromethyl)benzamide (4n)

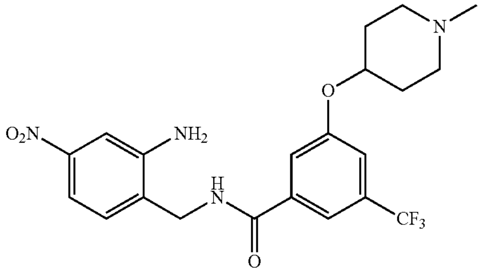 [SMILES: CN1CCC(Oc2cc(C(=O)NCc3ccc([N+](=O)[O-])cc3N)cc(C(F)(F)F)c2)CC1]

The compound was synthesized from Compound 3 using General Procedure A. A target Compound 4n (33%) was obtained as a solid; $^1$H NMR (400 MHz, DMSO-$d_6$) δ 9.30 (t, J=5.9 Hz, 1H), 7.83 (s, 1H), 7.79 (s, 1H), 7.52 (t, J=2.5 Hz, 2H), 7.38 (dd, J=8.3, 2.4 Hz, 1H), 7.25 (d, J=8.4 Hz, 1H), 5.83 (d, J=7.1 Hz, 2H), 4.72 (s, 1H), 4.41 (d, J=5.8 Hz, 2H), 3.32 (s, 3H), 2.85 (s, 2H), 2.40 (s, 2H), 2.05 (s, 2H), 1.79 (s, 2H); HRMS (ESI$^+$) calculated for $C_{16}H_{14}ClN_3O_3$ [M+H]$^+$: 453.1671, found 453.2374.

1-acetyl-N-(2-amino-4-nitrobenzyl)piperidine-4-carboxamide (4o)

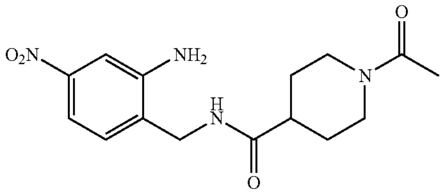 [SMILES: CC(=O)N1CCC(C(=O)NCc2ccc([N+](=O)[O-])cc2N)CC1]

The compound was synthesized from Compound 3 using General Procedure A. A target Compound 4o (67%) was obtained as a solid; $^1$H NMR (400 MHz, DMSO-$d_6$) δ 8.39 (t, J=6.0 Hz, 1H), 7.48 (d, J=2.4 Hz, 1H), 7.35 (dd, J=8.3, 2.4 Hz, 1H), 7.16 (d, J=8.3 Hz, 1H), 5.78-5.71 (m, 2H), 4.39-4.34 (m, 1H), 4.17 (d, J=6.1 Hz, 2H), 3.83 (d, J=13.7 Hz, 1H), 3.04 (dd, J=18.4, 7.6 Hz, 1H), 2.62-2.54 (m, 1H), 2.49-2.42 (m, 1H), 2.00 (s, 3H), 1.75 (t, J=13.4 Hz, 2H), 1.60-1.49 (m, 1H), 1.45-1.34 (m, 1H); HRMS (ESI$^+$) calculated for $C_{16}H_{14}ClN_3O_3$ [M+H]$^+$: 321.1485, found 321.7849.

N-(2-amino-4-nitrobenzyl)isonicotinamide (4p)

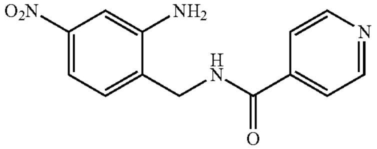 [SMILES: Nc1cc([N+](=O)[O-])ccc1CNC(=O)c1ccncc1]

The compound was synthesized from Compound 3 using General Procedure A. A target Compound 4p (60%) was obtained as a solid; $^1$H NMR (400 MHz, DMSO-$d_6$) δ 9.34 (t, J=5.9 Hz, 1H), 8.77 (dd, J=4.4, 1.7 Hz, 2H), 7.82 (dd, J=4.4, 1.7 Hz, 2H), 7.52 (d, J=2.4 Hz, 1H), 7.38 (dd, J=8.3, 2.4 Hz, 1H), 7.25 (d, J=8.4 Hz, 1H), 5.82 (d, J=7.1 Hz, 2H), 4.41 (d, J=6.0 Hz, 2H); HRMS (ESI$^+$) calculated for $C_{16}H_{14}ClN_3O_3$ [M+H]$^+$: 273.0909, found 273.3772.

N-(2-amino-4-nitrobenzyl)picolinamide (4q)

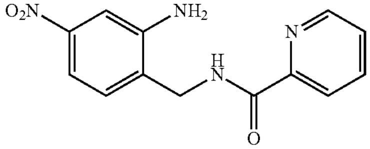 [SMILES: Nc1cc([N+](=O)[O-])ccc1CNC(=O)c1ccccn1]

The compound was synthesized from Compound 3 using General Procedure A. A target Compound 4q (70%) was obtained as a solid; $^1$H NMR (400 MHz, DMSO-$d_6$) δ 9.46 (t, J=6.3 Hz, 1H), 8.69 (ddd, J=4.8, 1.6, 1.0 Hz, 1H), 8.10-8.05 (m, 1H), 8.05-8.00 (m, 1H), 7.64 (ddd, J=7.3, 4.8, 1.5 Hz, 1H), 7.49 (d, J=2.4 Hz, 1H), 7.35 (dd, J=8.3, 2.4 Hz, 1H), 7.27 (d, J=8.3 Hz, 1H), 5.90 (s, 2H), 4.40 (d, J=6.4 Hz, 2H); HRMS (ESI$^+$) calculated for $C_{16}H_{14}ClN_3O_3$ [M+Na]$^+$: 295.0802, found 295.3123.

N-(2-amino-4-nitrobenzyl)-3,4-dichlorobenzamide (4r)

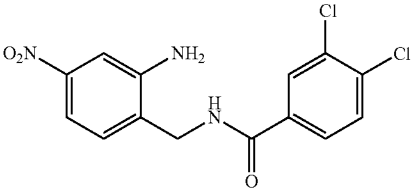 [SMILES: Nc1cc([N+](=O)[O-])ccc1CNC(=O)c1ccc(Cl)c(Cl)c1]

The compound was synthesized from Compound 3 using General Procedure A. A target Compound 4r (84.5%) was obtained as a solid; $^1$H NMR (400 MHz, DMSO) δ 8.23 (t, J=5.9 Hz, 1H), 7.15 (d, J=2.0 Hz, 1H), 6.89 (dd, J=8.4, 2.1 Hz, 1H), 6.81 (d, J=8.4 Hz, 1H), 6.52 (d, J=2.4 Hz, 1H), 6.37 (dd, J=8.3, 2.4 Hz, 1H), 6.24 (d, J=8.3 Hz, 1H), 4.82 (s, 2H), 3.39 (d, J=5.9 Hz, 2H).

N-(2-amino-4-nitrobenzyl)-2-(4-fluorophenyl)acetamide (4s)

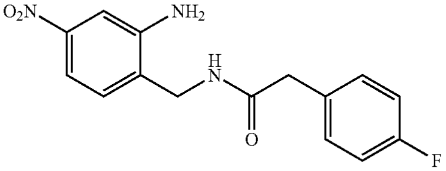 [SMILES: Nc1cc([N+](=O)[O-])ccc1CNC(=O)Cc1ccc(F)cc1]

The compound was synthesized from Compound 3 using General Procedure A. A target Compound 4s (33.0%) was obtained as a solid; $^1$H NMR (400 MHz, DMSO) δ 8.58 (t, J=6.0 Hz, 1H), 7.48 (d, J=2.4 Hz, 1H), 7.32 (tt, J=5.3, 2.6 Hz, 3H), 7.15 (ddd, J=9.7, 6.5, 2.7 Hz, 3H), 5.75 (s, 2H), 4.18 (d, J=6.1 Hz, 2H), 3.52 (s, 2H).

N-(2-amino-4-nitrobenzyl)-2-(2-(trifluoromethyl)phenyl)acetamide (4t)

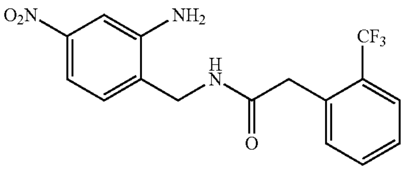 [SMILES: Nc1cc([N+](=O)[O-])ccc1CNC(=O)Cc1ccccc1C(F)(F)F]

The compound was synthesized from Compound 3 using General Procedure A. A target Compound 4t (32.0%) was obtained as a solid; $^1$H NMR (400 MHz, DMSO) δ 8.65 (t, J=6.0 Hz, 1H), 7.69 (s, 1H), 7.67 (s, 1H), 7.52 (s, 1H), 7.50

(s, 1H), 7.47 (d, J=2.4 Hz, 1H), 7.32 (dd, J=8.3, 2.4 Hz, 1H), 7.16 (d, J=8.3 Hz, 1H), 5.74 (s, 2H), 4.18 (d, J=6.0 Hz, 2H), 3.64 (s, 2H).

N-(2-amino-4-nitrobenzyl)-2-naphthamide (4u)

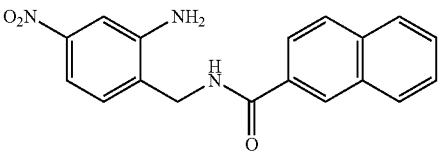 [SMILES: Nc1cc([N+](=O)[O-])ccc1CNC(=O)c1ccc2ccccc2c1]

The compound was synthesized from Compound 3 using General Procedure A. A target Compound 4u (41.5%) was obtained as a solid; $^{1}$H NMR (400 MHz, DMSO) δ 9.22 (t, J=5.9 Hz, 1H), 8.52 (s, 1H), 8.06-7.96 (m, 4H), 7.66-7.58 (m, 2H), 7.51 (d, J=2.4 Hz, 1H), 7.37 (dd, J=8.3, 2.4 Hz, 1H), 7.28 (d, J=8.3 Hz, 1H), 5.87 (s, 2H), 4.44 (d, J=6.0 Hz, 2H).

<Preparation Example 4> General Procedure B: Synthesis of Compounds 5a-l and 5n-u The following compounds were obtained by the method of Preparation Example 4.

4-(4-(7-nitroquinazolin-2-yl)-2-(trifluoromethyl) phenyl)morpholine (5a)

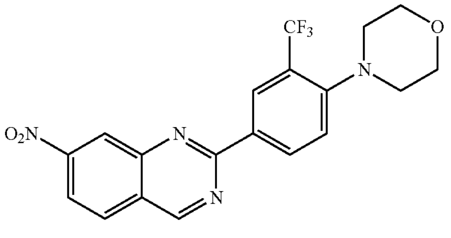 [SMILES: O=[N+]([O-])c1ccc2cnc(-c3ccc(N4CCOCC4)c(C(F)(F)F)c3)nc2c1]

The compound was synthesized from Compound 4a using General Procedure B. A target Compound 5a (62%) was obtained as a solid; $^{1}$H NMR (400 MHz, DMSO-$d_6$) δ 9.98 (d, J=0.8 Hz, 1H), 8.87 (d, J=1.9 Hz, 2H), 8.83 (dd, J=8.5, 2.0 Hz, 1H), 8.50 (dd, J=8.9, 0.5 Hz, 1H), 8.46 (dd, J=8.9, 2.1 Hz, 1H), 7.75 (d, J=8.5 Hz, 1H), 3.81-3.74 (m, 4H), 3.07-2.99 (m, 4H); HRMS (ESI$^+$) calculated for $C_{19}H_{15}F_3N_4O_3$ [M+H]$^+$: 405.1096, found 405.0978.

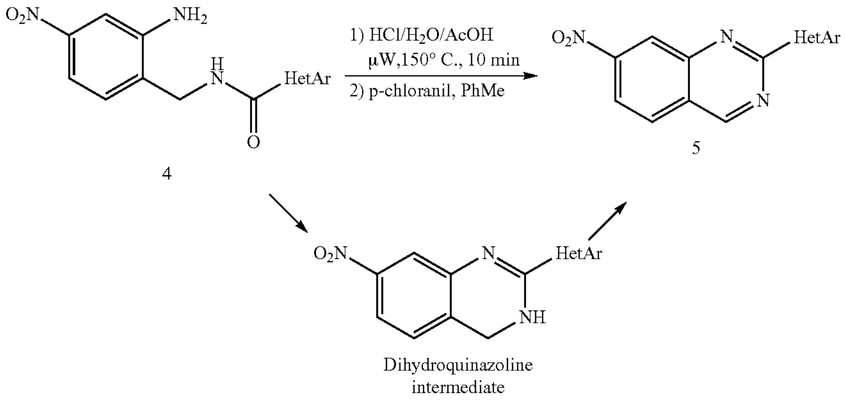

Compound 4 (0.2515 mmol) and conc aq HCl (1.2 eq) were taken out of a vial, slowly added dropwise to acetic acid (0.838 mL), and then reacted at 150° C. in a microwave environment for 10 minutes. After reaction, the mixture was neutralized with 1 N NaOH at 0° C. and cooled. When the product was precipitated upon neutralization, the product was filtered under vacuum and then dried to obtain a dihydroquinazoline intermediate without further purification. When the product was not precipitated, an organic layer was obtained by separating the layers with EA, and the remaining water was removed using anhydrous $Na_2SO_4$ and then filtered to obtain a dihydroquinazoline intermediate without further purification. Hereinafter, dihydroquinazoline (1 eq) and p-chloranil (1.2 eq) were stirred under reflux in toluene (0.1 M) overnight. After the reaction was confirmed, the resulting product was cooled and then concentrated under reduced pressure, the layers were separated with 0.5 N NaOH and dichloromethane or EA to obtain an organic layer, and then the remaining water was removed using anhydrous $Na_2SO_4$, and then the residue was filtered and purified through silica gel column chromatography to obtain Compound 5.

4-(3-(7-nitroquinazolin-2-yl)-5-(trifluoromethyl) phenyl)morpholine (5b)

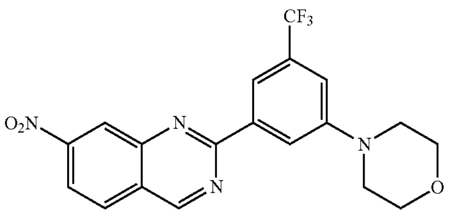 [SMILES: O=[N+]([O-])c1ccc2cnc(-c3cc(N4CCOCC4)cc(C(F)(F)F)c3)nc2c1]

The compound was synthesized from Compound 4b using General Procedure B. A target Compound 5b (57%) was obtained as a solid; $^{1}$H NMR (400 MHz, DMSO-$d_6$) δ 9.97 (d, J=0.7 Hz, 1H), 8.89 (d, J=2.1 Hz, 1H), 8.50 (d, J=8.6 Hz, 1H), 8.46 (dd, J=8.9, 2.1 Hz, 1H), 8.40 (s, 1H), 8.27 (s, 1H), 7.45 (s, 1H), 3.85-3.78 (m, 4H), 3.36-3.29 (m, 4H); HRMS (ESI$^+$) calculated for $C_{19}H_{15}F_3N_4O_3$ [M+H]$^+$: 405.1096, found 405.1609.

2-(3-(4-methyl-1H-imidazol-1-yl)-5-(trifluoromethyl)phenyl)-7-nitroquinazoline (5c)

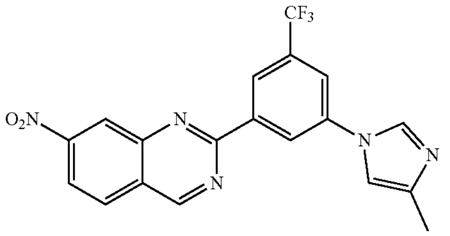 [SMILES: Cc1cn(-c2cc(-c3ncc4ccc([N+](=O)[O-])cc4n3)cc(C(F)(F)F)c2)cn1]

The compound was synthesized from Compound 4c using General Procedure B. A target Compound 5c (48%) was obtained as a solid; $^1$H NMR (400 MHz, DMSO-$d_6$) δ 10.05 (s, 1H), 8.97 (s, 2H), 8.78 (s, 1H), 8.58-8.48 (m, 3H), 8.29 (s, 1H), 7.77 (s, 1H), 2.24 (s, 3H); HRMS (ESI$^+$) calculated for $C_{19}H_{12}F_3N_5O_2$ $[M+H]^+$: 400.0943, found 400.1503.

2-(3-(4-methylpiperazin-1-yl)-5-(trifluoromethyl)phenyl)-7-nitroquinazoline (5d)

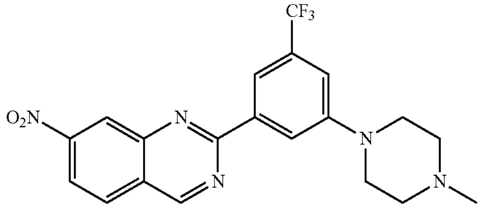 [SMILES: CN1CCN(c2cc(-c3ncc4ccc([N+](=O)[O-])cc4n3)cc(C(F)(F)F)c2)CC1]

The compound was synthesized from Compound 4d using General Procedure B. A target Compound 5d (41%) was obtained as a solid; $^1$H NMR (400 MHz, DMSO-$d_6$) δ 9.96 (d, J=0.8 Hz, 1H), 8.91-8.87 (m, 1H), 8.49 (dd, J=8.9, 0.5 Hz, 1H), 8.45 (dd, J=8.9, 2.1 Hz, 1H), 8.38 (s, 1H), 8.23 (s, 1H), 7.42 (s, 1H), 3.40-3.35 (m, 4H), 2.53 (d, J=5.0 Hz, 4H), 2.26 (s, 3H); HRMS (ESI$^+$) calculated for $C_{20}H_{18}F_3N_5O_2$ $[M+H]^+$: 418.1413, found 418.1756.

2-(3-((4-ethylpiperazin-1-yl)methyl)-5-(trifluoromethyl)phenyl)-7-nitroquinazoline (5e)

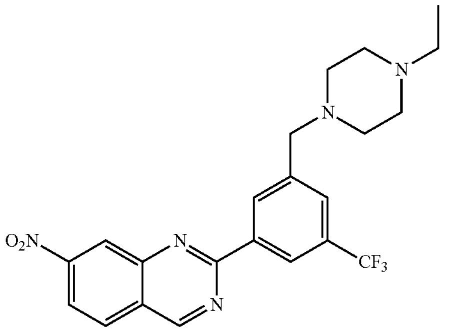 [SMILES: CCN1CCN(Cc2cc(-c3ncc4ccc([N+](=O)[O-])cc4n3)cc(C(F)(F)F)c2)CC1]

The compound was synthesized from Compound 4e using General Procedure B. A target Compound 5e (33%) was obtained as a solid; $^1$H NMR (400 MHz, $CDCl_3$) δ 9.68 (d, J=0.8 Hz, 1H), 9.05 (d, J=2.2 Hz, 1H), 8.87 (s, 1H), 8.81 (s, 1H), 8.45 (dd, J=8.8, 2.2 Hz, 1H), 8.19 (d, J=8.6 Hz, 1H), 7.85 (s, 1H), 3.75 (s, 2H), 2.63 (s, 4H), 2.54-2.47 (m, 2H), 1.64-1.58 (m, 4H), 1.14 (t, J=7.2 Hz, 3H); HRMS (ESL) calculated for $C_{22}H_{22}F_3N_5O_2$ $[M+H]^+$: 446.1726, found 446.8992.

2-(3-fluoro-5-(trifluoromethyl)phenyl)-7-nitroquinazoline (5f)

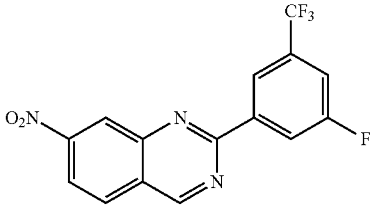 [SMILES: O=[N+]([O-])c1ccc2cnc(-c3cc(F)cc(C(F)(F)F)c3)nc2c1]

The compound was synthesized from Compound 4f using General Procedure B. A target Compound 5f (88%) was obtained as a solid; $^1$H NMR (400 MHz, DMSO-$d_6$) δ 10.02 (d, J=0.8 Hz, 1H), 8.94-8.89 (m, 1H), 8.71 (d, J=0.4 Hz, 1H), 8.60 (d, J=9.6 Hz, 1H), 8.53 (dd, J=8.9, 0.6 Hz, 1H), 8.49 (dd, J=8.9, 2.1 Hz, 1H), 7.99 (d, J=8.4 Hz, 1H); HRMS (ESI+) calculated for $C_{15}H_7F_4N_3O_2$ $[M+H]^+$: 338.0474, found 338.0284.

2-(4-chloro-3-(trifluoromethyl)phenyl)-7-nitroquinazoline (5g)

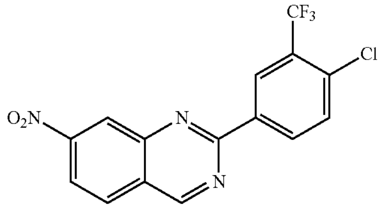 [SMILES: O=[N+]([O-])c1ccc2cnc(-c3ccc(Cl)c(C(F)(F)F)c3)nc2c1]

The compound was synthesized from Compound 4g using General Procedure B. A target Compound 5g (89%) was obtained as a solid; $^1$H NMR (400 MHz, $CDCl_3$) δ 9.67 (d, J=0.8 Hz, 1H), 9.07 (d, J=2.1 Hz, 1H), 9.03 (dd, J=1.5, 0.7 Hz, 1H), 8.82 (dd, J=8.4, 2.1 Hz, 1H), 8.46 (dd, J=8.9, 2.2 Hz, 1H), 8.22-8.17 (m, 1H), 7.74 (d, J=8.4 Hz, 1H); HRMS (ESI$^+$) calculated for $C_{15}H_7C_1F_3N_3O_2$ $[M+H]^+$: 354.0179, found 354.3435.

7-nitro-2-(1-phenyl-5-(trifluoromethyl)-1H-pyrazol-4-yl)quinazoline (5h)

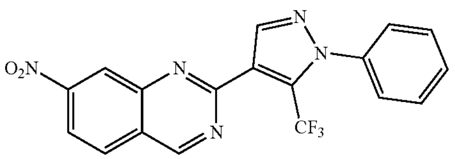 [SMILES: O=[N+]([O-])c1ccc2cnc(-c3cnn(-c4ccccc4)c3C(F)(F)F)nc2c1]

The compound was synthesized from Compound 4h using General Procedure B. A target Compound 5h (65%) was obtained as a solid; $^1H$ NMR (400 MHz, DMSO-$d_6$) δ 9.97 (d, J=0.8 Hz, 1H), 8.73 (dt, J=1.8, 0.8 Hz, 1H), 8.58-8.55 (m, 1H), 8.52-8.47 (m, 2H), 7.63 (s, 5H); HRMS (ESI$^+$) calculated for $C_{15}H_{10}F_3N_5O_2$ $[M+H]^+$: 386.0787, found 386.0962.

2-(3-chlorophenyl)-7-nitroquinazoline (5i)

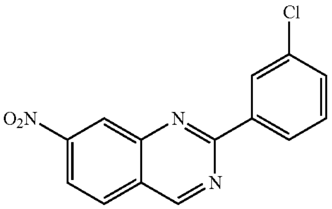 [SMILES: O=[N+]([O-])c1ccc2cnc(-c3cccc(Cl)c3)nc2c1]

The compound was synthesized from Compound 4i using General Procedure B. A target Compound 5i (78.6%) was obtained as a solid; $^1H$ NMR (400 MHz, $CDCl_3$) δ 9.66 (d, J=0.8 Hz, 1H), 9.01 (d, J=2.2 Hz, 1H), 8.70 (dd, J=2.5, 1.2 Hz, 1H), 8.59 (dt, J=7.2, 1.6 Hz, 1H), 8.43 (dd, J=8.9, 2.2 Hz, 1H), 8.19-8.15 (m, 1H), 7.57 (dt, J=8.0, 1.7 Hz, 1H), 7.54 (dd, J=11.3, 4.0 Hz, 1H); HRMS (ESI$^+$) calculated for $C_{14}H_8ClN_3O_2$ $[M+H]^+$: 286.0305, found 286.2357.

(E)-2-(4-methoxystyryl)-7-nitroquinazoline (5j)

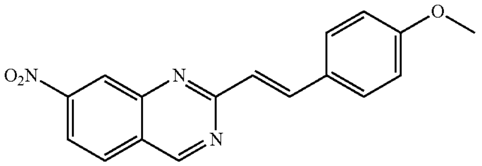 [SMILES: COc1ccc(/C=C/c2ncc3ccc([N+](=O)[O-])cc3n2)cc1]

The compound was synthesized from Compound 4j using General Procedure B. A target Compound 5j (34%) was obtained as a solid; $^1H$ NMR (400 MHz, DMSO-$d_6$) δ 9.81 (s, 1H), 8.69 (d, J=2.0 Hz, 1H), 8.42 (d, J=8.8 Hz, 1H), 8.38 (dd, J=8.9, 2.1 Hz, 1H), 8.19 (d, J=15.9 Hz, 1H), 7.80 (d, J=8.7 Hz, 2H), 7.36 (d, J=15.9 Hz, 1H), 7.04 (d, J=8.7 Hz, 2H), 3.84 (s, 3H); HRMS (ESI$^+$) calculated for $C_{17}H_{13}N_3O_3$ $[M+H]^+$: 308.0957, found 308.3506.

(E)-2-(4-chlorostyryl)-7-nitroquinazoline (5k)

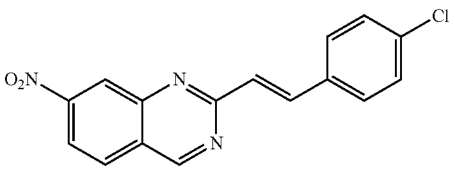

The compound was synthesized from Compound 4k using General Procedure B. A target Compound 5k (60%) was obtained as a solid; $^1H$ NMR (400 MHz, DMSO-$d_6$) δ 9.86 (s, 1H), 8.72 (d, J=2.0 Hz, 1H), 8.45 (d, J=8.9 Hz, 1H), 8.42 (dd, J=8.8, 2.1 Hz, 1H), 8.21 (d, J=16.0 Hz, 1H), 7.90 (m, 2H), 7.54 (m, 3H); HRMS (ESI$^+$) calculated for $C_{16}H_{10}ClN_3O_2$ $[M+H]^+$: 312.0462, found 312.2404.

5-(tert-butyl)-3-(7-nitroquinazolin-2-yl)isoxazole (5l)

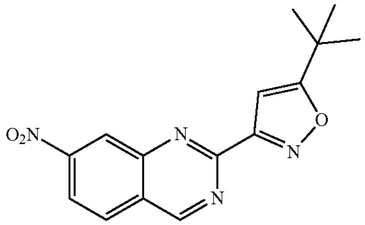 [SMILES: CC(C)(C)c1cc(-c2ncc3ccc([N+](=O)[O-])cc3n2)no1]

The compound was synthesized from Compound 4l using General Procedure B. A target Compound 5l (82%) was obtained as a solid; $^1H$ NMR (400 MHz, $CDCl_3$) δ 9.73 (d, J=0.6 Hz, 1H), 9.08 (dd, J=1.5, 0.7 Hz, 1H), 8.51 (dd, J=8.9, 2.2 Hz, 1H), 8.25-8.21 (m, 1H), 6.87 (d, J=4.5 Hz, 1H), 1.49 (s, 9H); HRMS (ESI$^+$) calculated for $C_{15}H_{14}N_4O_3$ $[M+H]^+$: 299.1066, found 299.0941.

<Preparation Example 5> General Procedure C: Synthesis of Compounds 5m and 5v

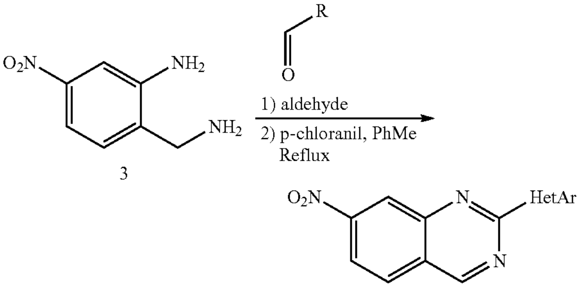

3

5m, 5v

Compound 3 (1.326 mmol) and carbaldehyde (1.194 mmol) were dissolved in THF (13.26 ml, 0.1 M), and the resulting solution was stirred at room temperature for 16 hours. After it was confirmed through TLC that Compound 3 was completely consumed, p-chloranil (1.618 mmol) was added to the reaction solution, and the resulting solution was stirred at 65° C. for 12 hours. After the reaction was confirmed, the resulting product was cooled and then concentrated under reduced pressure, the layers were separated with 0.5 N NaOH and dichloromethane or EA to obtain an organic layer, and then the remaining water was removed using anhydrous $Na_2SO_4$, and then the residue was filtered and purified through silica gel column chromatography to obtain Compounds 5m and 5v as solids.

The following compounds were obtained by the method of Preparation Example 5.

2-(1H-indazol-5-yl)-7-nitroquinazoline (5m)

5m

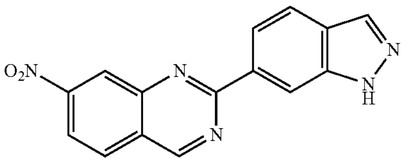

The compound was synthesized from Compound 3 using General Procedure C. A target Compound 5m (42%) was obtained as a solid; $^1$H NMR (400 MHz, DMSO-$d_6$) δ 13.43 (s, 1H), 9.97 (s, 1H), 8.85 (s, 1H), 8.82 (s, 1H), 8.49 (d, J=8.8 Hz, 1H), 8.44 (dd, J=8.9, 1.9 Hz, 1H), 8.40 (d, J=8.5 Hz, 1H), 8.20 (s, 1H), 7.97 (d, J=8.5 Hz, 1H); HRMS (ESI$^+$) calculated for $C_{15}H_9N_5O_2$ [M+H]$^+$: 292.0756, found 292.3588.

2-(3-((1-methylpiperidin-4-yl)oxy)-5-(trifluoromethyl)phenyl)-7-nitroquinazoline (5n)

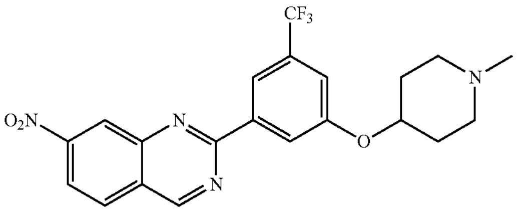 [SMILES: CN1CCC(Oc2cc(-c3ncc4ccc([N+](=O)[O-])cc4n3)cc(C(F)(F)F)c2)CC1]

The compound was synthesized from Compound 4n using General Procedure B. A target Compound 5n (53%) was obtained as a solid; $^1$H NMR (400 MHz, $CDCl_3$) δ 9.67 (d, J=0.8 Hz, 1H), 9.04 (d, J=2.2 Hz, 1H), 8.57 (s, 1H), 8.45 (dd, J=8.9, 2.2 Hz, 1H), 8.43 (s, 1H), 8.19 (d, J=8.9 Hz, 1H), 7.36 (s, 1H), 4.63 (s, 1H), 2.78 (s, 2H), 2.47 (s, 2H), 2.40 (s, 3H), 2.21 (s, 1H), 2.16 (dd, J=13.1, 3.7 Hz, 2H), 2.04-1.95 (m, 2H); HRMS (ESI$^+$) calculated for $C_{21}H_{19}F_3N_4O_3$ [M+H]$^+$: 433.1409, found 433.7546.

1-(4-(7-nitroquinazolin-2-yl)piperidin-1-yl)ethan-1-one (5o)

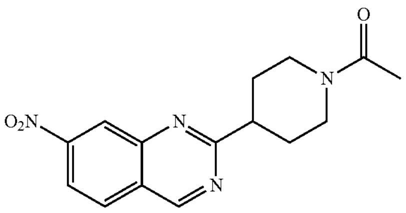 [SMILES: CC(=O)N1CCC(c2ncc3ccc([N+](=O)[O-])cc3n2)CC1]

The compound was synthesized from Compound 4o using General Procedure B. A target Compound 5o (30%) was obtained as a solid; $^1$H NMR (400 MHz, $CDCl_3$) δ 9.55 (d, J=0.8 Hz, 1H), 8.91 (d, J=2.2 Hz, 1H), 8.42 (dd, J=8.9, 2.2 Hz, 1H), 8.16-8.12 (m, 1H), 4.82-4.74 (m, 1H), 4.03 (d, J=13.5 Hz, 1H), 3.39 (ddd, J=15.1, 7.6, 3.6 Hz, 1H), 3.32 (dt, J=13.6, 4.0 Hz, 1H), 2.87 (td, J=12.8, 2.9 Hz, 1H), 2.26-2.20 (m, 2H), 2.20 (s, 3H), 2.14-2.05 (m, 1H), 1.96 (ddd, J=25.6, 12.1, 4.3 Hz, 1H); HRMS (ESI$^+$) calculated for $C_{15}H_{16}N_4O_3$ [M+H]$^+$: 301.1222, found 301.4713.

7-nitro-2-(pyridin-4-yl)quinazoline (5p)

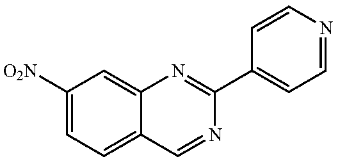 [SMILES: O=[N+]([O-])c1ccc2cnc(-c3ccncc3)nc2c1]

The compound was synthesized from Compound 4p using General Procedure B. A target Compound 5p (11%) was obtained as a solid; $^1$H NMR (400 MHz, $CDCl_3$) δ 9.72 (d, J=0.8 Hz, 1H), 9.05 (dd, J=1.5, 0.7 Hz, 1H), 8.89 (dd, J=4.6, 1.5 Hz, 2H), 8.55 (dd, J=4.5, 1.6 Hz, 2H), 8.49 (dd, J=8.9, 2.2 Hz, 1H), 8.26-8.20 (m, 1H); HRMS (ESI+) calculated for $C_{13}H_8N_4O_2$ [M+H]$^+$: 253.0647, found 253.2785.

7-nitro-2-(pyridin-2-yl)quinazoline (5q)

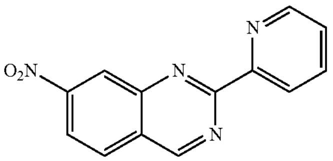 [SMILES: O=[N+]([O-])c1ccc2cnc(-c3ccccn3)nc2c1]

The compound was synthesized from Compound 4q using General Procedure B. A target Compound 5q (35%) was obtained as a solid; $^1$H NMR (400 MHz, $CDCl_3$) δ 9.79 (s, 1H), 9.18 (d, J=2.1 Hz, 1H), 9.01 (d, J=4.0 Hz, 1H), 8.80 (d, J=7.9 Hz, 1H), 8.49 (dd, J=8.9, 2.2 Hz, 1H), 8.26-8.21 (m, 1H), 8.03 (td, J=7.8, 1.7 Hz, 1H), 7.59-7.54 (m, 1H); HRMS (ESI$^+$) calculated for $C_{13}H_8N_4O_2$ [M+H]$^+$: 253.0647, found 253.2424.

2-(3,4-dichlorophenyl)-7-nitroquinazoline (5r)

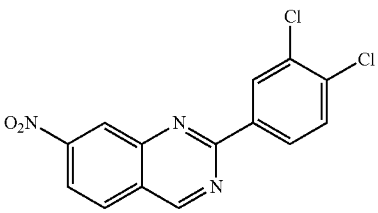 [SMILES: O=[N+]([O-])c1ccc2cnc(-c3ccc(Cl)c(Cl)c3)nc2c1]

The compound was synthesized from Compound 4r using General Procedure B. A target Compound 5r (61%) was obtained as a solid; $^1$H NMR (400 MHz, DMSO) δ 9.99 (d, J=0.8 Hz, 1H), 8.91-8.86 (m, 1H), 8.74 (d, J=2.0 Hz, 1H), 8.55 (dd, J=8.5, 2.0 Hz, 1H), 8.51 (d, J=8.3 Hz, 1H), 8.48 (dd, J=8.9, 2.0 Hz, 1H), 7.91 (d, J=8.5 Hz, 1H).

2-(4-fluorobenzyl)-7-nitroquinazoline (5s)

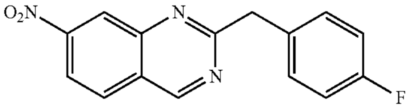 [SMILES: O=[N+]([O-])c1ccc2cnc(Cc3ccc(F)cc3)nc2c1]

The compound was synthesized from Compound 4s using General Procedure B. A target Compound 5s (59%) was obtained as a solid; $^1$H NMR (400 MHz, $CDCl_3$) δ 9.53 (d, J=0.7 Hz, 1H), 8.93 (d, J=2.1 Hz, 1H), 8.41 (dd, J=8.9, 2.2 Hz, 1H), 8.12 (d, J=8.9 Hz, 1H), 7.47-7.41 (m, 2H), 7.08-7.01 (m, 2H), 4.50 (s, 2H).

7-nitro-2-(2-(trifluoromethyl)benzyl)quinazoline (5t)

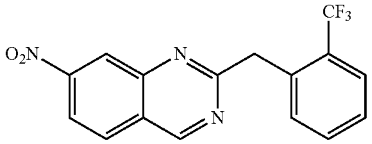 [SMILES: O=[N+]([O-])c1ccc2cnc(Cc3ccccc3C(F)(F)F)nc2c1]

The compound was synthesized from Compound 4t using General Procedure B. A target Compound 5t (31.4%) was obtained as a solid; $^1$H NMR (400 MHz, $CDCl_3$) δ 9.48 (s, 1H), 8.87 (d, J=1.8 Hz, 1H), 8.36 (dd, J=8.9, 2.1 Hz, 1H), 8.07 (d, J=8.9 Hz, 1H), 7.58-7.51 (m, 4H), 4.53 (s, 2H).

2-(naphthalen-2-yl)-7-nitroquinazoline (5u)

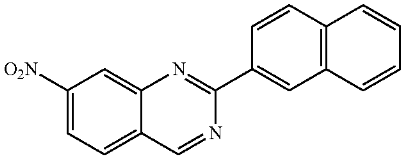 [SMILES: O=[N+]([O-])c1ccc2cnc(-c3ccc4ccccc4c3)nc2c1]

The compound was synthesized from Compound 4u using General Procedure B. A target Compound 5u (49%) was obtained as a solid; $^1$H NMR (400 MHz, $CDCl_3$) δ 9.66 (s, 1H), 9.22 (s, 1H), 9.02 (d, J=1.8 Hz, 1H), 8.74 (dd, J=8.6, 1.6 Hz, 1H), 8.38 (dd, J=8.8, 2.1 Hz, 1H), 8.13 (d, J=8.9 Hz, 1H), 8.08-8.04 (m, 1H), 8.02 (d, J=8.7 Hz, 1H), 7.92 (d, J=7.0 Hz, 1H), 7.61-7.54 (m, 2H).

2-(2,3-dihydrobenzofuran-5-yl)-7-nitroquinazoline (5v)

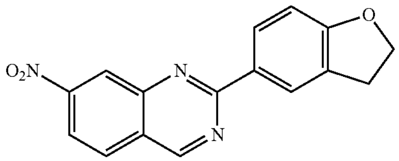

The compound was synthesized from Compound 3 using General Procedure C. A target Compound 5v (43%) was obtained as a solid; $^1$H NMR (400 MHz, $CDCl_3$) δ 9.57 (d, J=0.8 Hz, 1H), 8.93 (d, J=2.2 Hz, 1H), 8.59-8.51 (m, 2H), 8.34 (dd, J=8.8, 2.2 Hz, 1H), 8.10 (d, J=8.8 Hz, 1H), 6.98 (d, J=8.4 Hz, 1H), 4.74 (dd, J=10.3, 7.2 Hz, 2H), 3.38 (t, J=8.7 Hz, 2H).

<Preparation Example 6> General Procedure D: Synthesis of Compound 6a-q

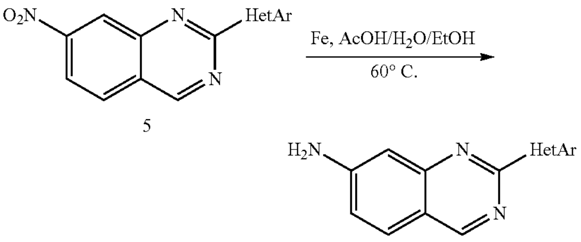

5

6

Compound 5 (1 eq) was dissolved in EtOH/AcOH/$H_2O$ (2:2:1, 0.1 M), Fe (5 eq) was added thereto, and the resulting mixture was stirred at 60° C. for 1 hour. After the mixture was cooled at room temperature, the solvent was distilled under reduced pressure and filtered through Celite, and layers were separated under basic conditions using EtOAC and 1 M NaOH. An organic layer was obtained and subjected to layer separation with saturated NaCl (brine) again, an organic layer was obtained and the remaining water was removed with anhydrous $Na_2SO_4$ to obtain Compound 6.

The following compounds were obtained by the method of Preparation Example 6.

2-(4-morpholino-3-(trifluoromethyl)phenyl)quinazoline-7-amine (6a)

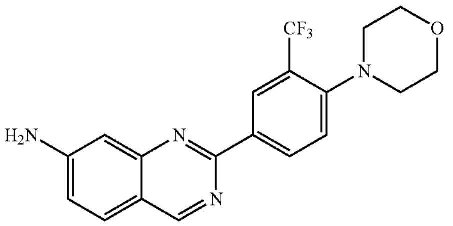

The compound was synthesized from Compound 5a using General Procedure D. A target Compound 6a (47%) was obtained as a solid; $^1$H NMR (400 MHz, DMSO-$d_6$) δ 9.15 (d, J=0.6 Hz, 1H), 8.77 (d, J=2.0 Hz, 1H), 8.72 (dd, J=8.4, 1.9 Hz, 1H), 7.78 (d, J=8.8 Hz, 1H), 7.68 (d, J=8.5 Hz, 1H), 7.07 (dd, J=8.8, 2.1 Hz, 1H), 6.87 (d, J=2.0 Hz, 1H), 6.52 (s, 2H), 3.80-3.73 (m, 4H), 3.00-2.95 (m, 4H); HRMS (ESI$^+$) calculated for $C_{19}H_{17}F_3N_{40}$ $[M+H]^+$: 375.1354, found 375.0339.

2-(3-morpholino-5-(trifluoromethyl)phenyl)quinazoline-7-amine (6b)

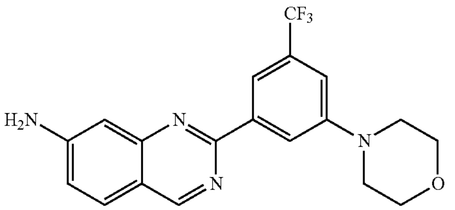

The compound was synthesized from Compound 5b using General Procedure D. A target Compound 6b (83%) was obtained as a solid; $^1$H NMR (400 MHz, DMSO-$d_6$) δ 9.14 (d, J=0.5 Hz, 1H), 8.30 (s, 1H), 8.18 (s, 1H), 7.78 (d, J=8.8 Hz, 1H), 7.35 (s, 1H), 7.06 (dd, J=8.8, 2.1 Hz, 1H), 6.86 (d, J=2.0 Hz, 1H), 6.51 (s, 2H), 3.82-3.78 (m, 4H), 3.32-3.28 (m, 4H); HRMS (ESI$^+$) calculated for $C_{19}H_{17}F_3N_{40}$ $[M+H]^+$: 375.1354, found 375.3806.

2-(3-(4-methyl-1H-imidazol-1-yl)-5-(trifluoromethyl)phenyl)quinazoline-7-amine (6c)

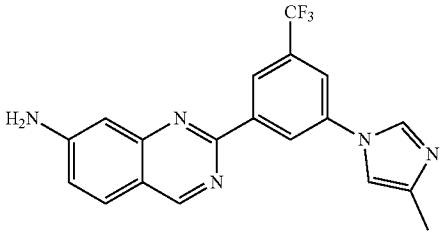

The compound was synthesized from Compound 5c using General Procedure D. A target Compound 6c (100%) was obtained as a solid; $^1$H NMR (400 MHz, $CDCl_3$) δ 9.20 (s, 1H), 8.81 (s, 1H), 8.67 (s, 1H), 8.38 (s, 1H), 8.15 (s, 1H), 7.82 (d, J=8.7 Hz, 1H), 7.69 (s, 1H), 7.10 (d, J=8.6 Hz, 1H), 6.90 (s, 1H), 6.59 (s, 2H), 2.20 (s, 3H); HRMS (ESI$^+$) calculated for $C_{19}H_{14}F_3N_5$ $[M+H]^+$: 370.1201, found 370.2122.

2-(3-(4-methylpiperazin-1-yl)-5-(trifluoromethyl)phenyl)quinazoline-7-amine (6d)

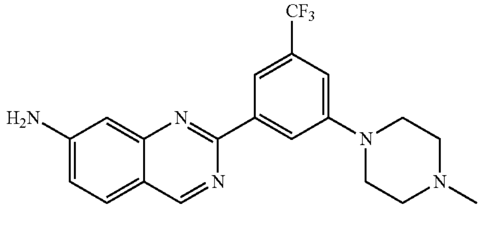

The compound was synthesized from Compound 5d using General Procedure D. A target Compound 6d (80%) was obtained as a solid; $^1$H NMR (400 MHz, DMSO-$d_6$) δ 9.16 (s, 1H), 8.32 (s, 1H), 8.17 (s, 1H), 7.79 (d, J=8.8 Hz, 1H), 7.34 (s, 1H), 7.08 (dd, J=8.8, 2.1 Hz, 1H), 6.88 (d, J=1.9 Hz, 1H), 6.52 (s, 2H), 3.30 (m, 4H), 2.54 (m, 4H), 2.27 (s, 3H); HRMS (ESI$^+$) calculated for $C_{20}H_{20}F_3N_5$ $[M+H]^+$: 388.1671, found 388.3958.

2-(3-((4-ethylpiperazin-1-yl)methyl)-5-(trifluoromethyl)phenyl)quinazoline-7-amine (6e)

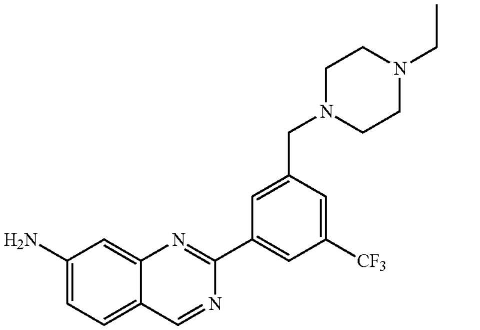

The compound was synthesized from Compound 5e using General Procedure D. The compound was purified by column chromatography (MC:Methanol=15:1) to obtain a target Compound 6e (33%) was obtained as a solid; IE NMR (400 MHz, DMSO-$d_6$) δ 9.18 (s, 1H), 8.71 (s, 1H), 8.66 (s, 1H), 7.81 (d, J=8.8 Hz, 1H), 7.77 (s, 1H), 7.09 (dd, J=8.8, 2.1 Hz, 1H), 6.89 (d, J=2.1 Hz, 1H), 6.54 (d, J=3.7 Hz, 2H), 3.69 (s, 2H), 3.31 (s, 4H), 2.46 (s, 4H), 2.36-2.30 (m, 2H), 1.00 (t, J=7.2 Hz, 3H); HRMS (ESI$^+$) calculated for $C_{18}H_{14}F_3N_5$ $[M+H]^+$: 416.1984, found 416.8992.

2-(3-fluoro-5-(trifluoromethyl)phenyl)quinazoline-7-amine (6f)

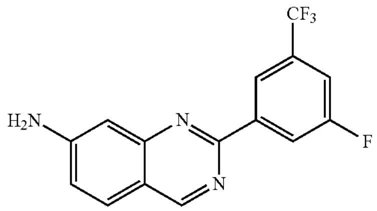

The compound was synthesized from Compound 5f using General Procedure D. A target Compound 6f (89%) was obtained as a solid; IE NMR (400 MHz, DMSO-$d_6$) δ 9.17 (d, J=0.6 Hz, 1H), 8.61 (s, 1H), 8.47 (d, J=10.0 Hz, 1H), 7.85 (d, J=8.4 Hz, 1H), 7.81 (d, J=8.8 Hz, 1H), 7.10 (dd, J=8.8, 2.1 Hz, 1H), 6.88 (d, J=2.0 Hz, 1H), 6.58 (s, 2H); HRMS (ESI$^+$) calculated for $C_{15}H_9F_4N_3$ $[M+H]^+$: 308.0733, found 308.3506.

2-(4-chloro-3-(trifluoromethyl)phenyl)quinazoline-7-amine (6g)

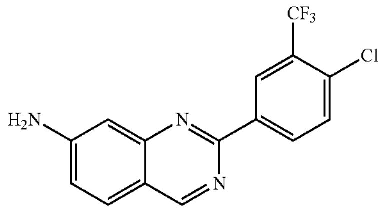

The compound was synthesized from Compound 5g using General Procedure D. A target Compound 6g (97%) was obtained as a solid; $^1$H NMR (400 MHz, DMSO-$d_6$) δ 9.16 (d, J=0.6 Hz, 1H), 8.87 (d, J=2.0 Hz, 1H), 8.73 (dd, J=8.5, 2.0 Hz, 1H), 7.89 (d, J=8.5 Hz, 1H), 7.79 (d, J=8.8 Hz, 1H), 7.08 (dd, J=8.8, 2.1 Hz, 1H), 6.87 (d, J=2.1 Hz, 1H), 6.56 (s, 2H); HRMS (ESI$^+$) calculated for $C_{15}H_9C_1F_3N_3$ [M+H]$^+$: 324.0437, found 324.1620.

2-(1-phenyl-5-(trifluoromethyl)-1H-pyrazol-4-yl)quinazoline-7-amine (6h)

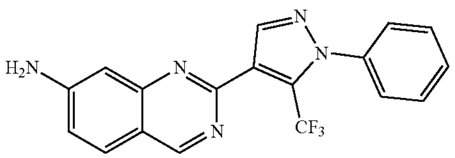 [SMILES: Nc1ccc2cnc(-c3cnn(-c4ccccc4)c3C(F)(F)F)nc2c1]

The compound was synthesized from Compound 5h using General Procedure D. A target Compound 6h (86%) was obtained as a solid; $^1$H NMR (400 MHz, DMSO-$d_6$) δ 9.11 (d, J=0.6 Hz, 1H), 8.36 (s, 1H), 7.77 (d, J=8.8 Hz, 1H), 7.60 (d, J=1.7 Hz, 5H), 7.07 (dd, J=8.8, 2.1 Hz, 1H), 6.81 (d, J=2.1 Hz, 1H), 6.50 (s, 2H); HRMS (ESI$^+$) calculated for $C_{15}H_{12}F_3N_5$ [M+H]$^+$: 356.1045, found 356.2275.

2-(3-chlorophenyl)quinazoline-7-amine (6i)

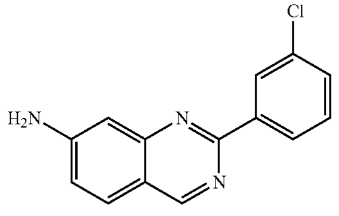

The compound was synthesized from Compound 5i using General Procedure D. A target Compound 6i (98%) was obtained as a solid; $^1$H NMR (400 MHz, DMSO-$d_6$) δ 9.15 (d, J=0.6 Hz, 1H), 8.49-8.42 (m, 2H), 7.79 (d, J=8.8 Hz, 1H), 7.62-7.54 (m, 2H), 7.08 (dd, J=8.8, 2.1 Hz, 1H), 6.86 (d, J=2.1 Hz, 1H), 6.52 (s, 2H); HRMS (ESI$^+$) calculated for $C_{14}H_{10}ClN_3$ [M+H]$^+$: 256.0563, found 256.0520.

(E)-2-(4-methoxystyryl)quinazoline-7-amine (6j)

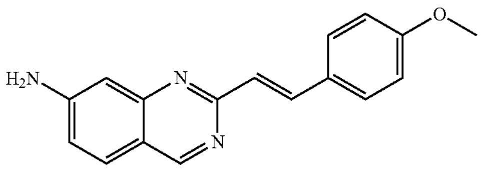

The compound was synthesized from Compound 5j using General Procedure D. A target Compound 6j (80%) was obtained as a solid; $^1$H NMR (400 MHz, DMSO-$d_6$) δ 8.99 (s, 1H), 7.92 (d, J=16.0 Hz, 1H), 7.68 (dd, J=8.8, 2.2 Hz, 3H), 7.12 (d, J=16.0 Hz, 1H), 6.98 (dd, J=8.6, 6.2 Hz, 3H), 6.74 (d, J=2.0 Hz, 1H), 6.35 (s, 2H), 3.80 (s, 3H); HRMS (ESI$^+$) calculated for $C_{17}H_{15}N_{30}$ [M+H]$^+$: 278.1215, found 278.3117.

(E)-2-(4-chlorostyryl)quinazoline-7-amine (6k)

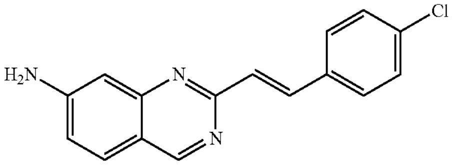 [SMILES: Nc1ccc2cnc(/C=C/c3ccc(Cl)cc3)nc2c1]

The compound was synthesized from Compound 5k using General Procedure D. A target Compound 6k (83%) was obtained as a solid; $^1$H NMR (400 MHz, DMSO-$d_6$) δ 9.04 (s, 1H), 7.96 (d, J=16.0 Hz, 1H), 7.79 (d, J=8.4 Hz, 2H), 7.73 (d, J=8.7 Hz, 1H), 7.49 (d, J=8.4 Hz, 2H), 7.30 (d, J=16.0 Hz, 1H), 7.07-6.98 (m, 1H), 6.78 (s, 1H), 6.41 (s, 2H); HRMS (ESI$^+$) calculated for $C_{16}H_{12}ClN_3$ [M+H]$^+$: 282.0720, found 282.2737.

2-(5-(tert-butyl)isoxazol-3-yl)quinazoline-7-amine (6l)

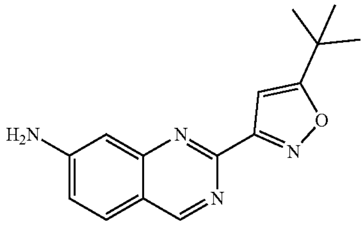

The compound was synthesized from Compound 5l using General Procedure D. A target Compound 6l (88%) was obtained as a solid; $^1$H NMR (400 MHz, DMSO-$d_6$) δ 9.13 (s, 1H), 7.80 (d, J=8.8 Hz, 1H), 7.11 (dd, J=8.8, 2.1 Hz, 1H), 6.84 (d, J=2.0 Hz, 1H), 6.77 (s, 1H), 6.58 (s, 2H), 1.38 (s, 9H); HRMS (ESI$^+$) calculated for $C_{15}H_{16}N_{40}$ [M+H]$^+$: 269.1324, found 269.1630.

2-(1H-indazol-5-yl)quinazoline-7-amine (6m)

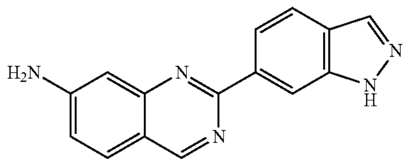 [SMILES: Nc1ccc2cnc(-c3ccc4cn[nH]c4c3)nc2c1]

The compound was synthesized from Compound 5m using General Procedure D. A target Compound 6m (74%) was obtained as a solid; $^1$H NMR (400 MHz, DMSO-$d_6$) δ 13.25 (s, 1H), 9.16 (s, 1H), 8.69 (d, J=0.9 Hz, 1H), 8.31 (dd, J=8.5, 1.3 Hz, 1H), 8.14 (d, J=1.1 Hz, 1H), 7.87 (d, J=8.5 Hz, 1H), 7.78 (d, J=8.7 Hz, 1H), 7.05 (dd, J=8.7, 2.1 Hz, 1H), 6.88 (d, J=2.1 Hz, 1H), 6.45 (d, J=4.1 Hz, 2H); HRMS (ESI$^+$) calculated for $C_{15}H_{11}N_5$ [M+H]$^+$: 262.1014, found 262.3553.

2-(3-((1-methylpiperidin-4-yl)oxy)-5-(trifluoromethyl)phenyl)quinazoline-7-amine (6n)

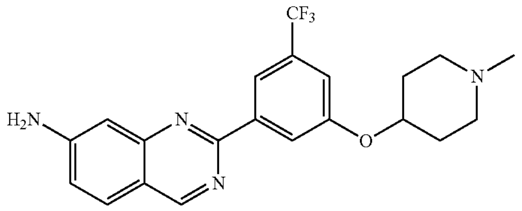

The compound was synthesized from Compound 5n using General Procedure D. A target Compound 6n (100%) was obtained as a solid; $^1$H NMR (400 MHz, DMSO-$d_6$) δ 9.17 (s, 1H), 8.34 (s, 1H), 8.28 (s, 1H), 7.80 (d, J=8.8 Hz, 1H), 7.41 (s, 1H), 7.09 (dd, J=8.8, 2.1 Hz, 1H), 6.88 (d, J=2.0 Hz, 1H), 6.54 (s, 2H), 4.69-4.61 (m, 1H), 2.63 (d, J=5.6 Hz, 2H), 2.27 (t, J=8.7 Hz, 2H), 2.22 (s, 3H), 1.99 (s, 2H), 1.79-1.68 (m, 2H); HRMS (ESI$^+$) calculated for $C_{21}H_{21}F_3N_{40}$ [M+H]$^+$: 403.1667, found 403.5034.

1-(4-(7-aminoquinazolin-2-yl)piperidin-1-yl)ethane-1-one (6o)

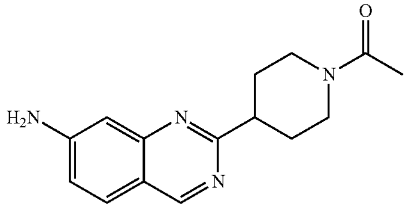

The compound was synthesized from Compound 5o using General Procedure D. A target Compound 6o (83%) was obtained as a solid; $^1$H NMR (400 MHz, DMSO-$d_6$) δ 8.98 (s, 1H), 7.70 (t, J=6.4 Hz, 1H), 7.00 (dd, J=8.8, 2.1 Hz, 1H), 6.72 (d, J=2.1 Hz, 1H), 6.36 (s, 2H), 4.46 (d, J=13.1 Hz, 1H), 3.92 (d, J=13.6 Hz, 1H), 3.24-3.16 (m, 1H), 3.05 (tt, J=11.4, 3.8 Hz, 1H), 2.75-2.67 (m, 1H), 2.06-2.03 (m, 3H), 1.96 (dd, J=24.1, 7.7 Hz, 2H), 1.80 (ddd, J=25.0, 12.5, 4.3 Hz, 1H), 1.64 (ddd, J=16.5, 12.6, 4.4 Hz, 1H); HRMS (ESI$^+$) calculated for $C_{15}H_{18}N_4O$ [M+H]$^+$: 271.1481, found 271.4682.

2-(pyridin-4-yl)quinazoline-7-amine (6p)

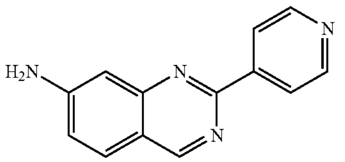

The compound was synthesized from Compound 5p using General Procedure D. A target Compound 6p (96%) was obtained as a solid; $^1$H NMR (400 MHz, DMSO-$d_6$) δ 9.20 (d, J=0.6 Hz, 1H), 8.76 (dd, J=4.5, 1.6 Hz, 2H), 8.35 (dd, J=4.5, 1.6 Hz, 2H), 7.82 (d, J=8.8 Hz, 1H), 7.12 (dd, J=8.8, 2.1 Hz, 1H), 6.90 (d, J=2.1 Hz, 1H), 6.58 (s, 2H); HRMS (ESI$^+$) calculated for $C_{13}H_{10}N_4$ [M+H]$^+$: 223.0905, found 223.3095.

2-(pyridin-2-yl)quinazoline-7-amine (6q)

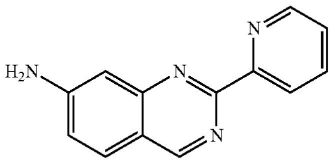

The compound was synthesized from Compound 5q using General Procedure D. A target Compound 6q (84%) was obtained as a solid; $^1$H NMR (400 MHz, $CDCl_3$) δ 9.26 (d, J=0.6 Hz, 1H), 8.90 (ddd, J=4.8, 1.8, 0.9 Hz, 1H), 8.65 (dt, J=8.0, 1.0 Hz, 1H), 7.90 (td, J=7.8, 1.8 Hz, 1H), 7.76 (d, J=8.7 Hz, 1H), 7.42 (ddd, J=7.5, 4.8, 1.2 Hz, 1H), 7.25 (d, J=2.2 Hz, 1H), 7.04 (dd, J=8.7, 2.2 Hz, 1H), 4.46 (d, J=14.2 Hz, 2H); HRMS (ESI$^+$) calculated for $C_{13}H_{10}N_4$ [M+H]$^+$: 223.0905, found 223.1655.

2-(3,4-dichlorophenyl)quinazoline-7-amine (6r)

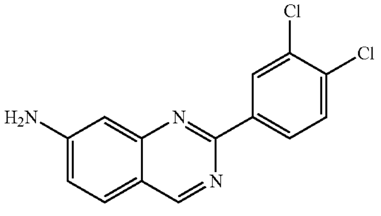

The compound was synthesized from Compound 5r using General Procedure D. A target Compound 6r (88.9%) was obtained as a solid; $^1$H NMR (400 MHz, DMSO) δ 9.14 (s, 1H), 8.60 (d, J=2.0 Hz, 1H), 8.43 (dd, J=8.5, 2.0 Hz, 1H), 7.78 (dd, J=8.6, 3.4 Hz, 2H), 7.07 (dd, J=8.8, 2.1 Hz, 1H), 6.84 (d, J=2.0 Hz, 1H), 6.54 (s, 2H).

2-(4-fluorobenzyl)quinazoline-7-amine (6s)

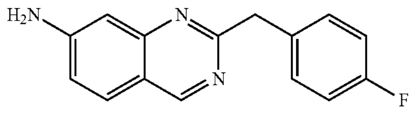

The compound was synthesized from Compound 5s using General Procedure D. A target Compound 6s (100%) was obtained as a solid. The corresponding compound was used for the next step reaction without further purification process.

2-(2-(trifluoromethyl)benzyl)quinazoline-7-amine (6t)

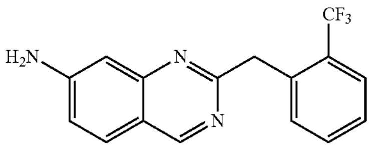

The compound was synthesized from Compound 5t using General Procedure D. A target Compound 6t (100%) was obtained as a solid. The corresponding compound was used for the next step reaction without further purification process; $^1$H NMR (400 MHz, DMSO) δ 8.94 (s, 1H), 7.68 (d, J=8.8 Hz, 1H), 7.64 (d, J=8.1 Hz, 2H), 7.54 (d, J=8.1 Hz, 2H), 6.99 (dd, J=8.8, 2.1 Hz, 1H), 6.72 (d, J=1.8 Hz, 1H), 6.39 (s, 2H), 4.27 (s, 2H).

2-(naphthalen-2-yl)quinazoline-7-amine (6u)

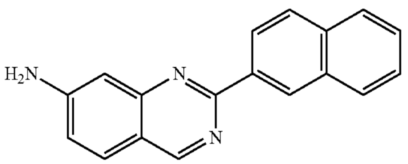

The compound was synthesized from Compound 5u using General Procedure D. A target Compound 6u (78%) was obtained as a solid. The corresponding compound was used for the next step reaction without further purification process; $^1$H NMR (400 MHz, DMSO) δ 9.18 (d, J=0.6 Hz, 1H), 9.07 (s, 1H), 8.62 (dd, J=8.6, 1.7 Hz, 1H), 8.14-8.11 (m, 1H), 8.03 (d, J=8.8 Hz, 1H), 7.99-7.96 (m, 1H), 7.78 (d, J=8.7 Hz, 1H), 7.61-7.55 (m, 2H), 7.05 (dd, J=8.7, 2.1 Hz, 1H), 6.90 (d, J=2.1 Hz, 1H), 6.47 (s, 2H).

2-(2,3-dihydrobenzofuran-5-yl)quinazoline-7-amine (6v)

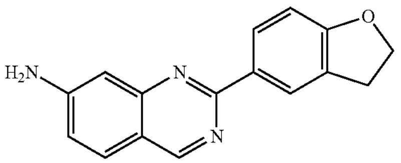 [SMILES: Nc1ccc2cnc(-c3ccc4c(c3)CCO4)nc2c1]

The compound was synthesized from Compound 5v using General Procedure D. A target Compound 6v (77.1%) was obtained as a solid. The corresponding compound was used for the next step reaction without further purification process; $^1$H NMR (400 MHz, DMSO) δ 9.05 (d, J=0.6 Hz, 1H), 8.36 (d, J=1.3 Hz, 1H), 8.28 (dd, J=8.4, 1.9 Hz, 1H), 7.69 (d, J=8.7 Hz, 1H), 6.97 (dd, J=8.7, 2.1 Hz, 1H), 6.86 (d, J=8.4 Hz, 1H), 6.78 (d, J=2.1 Hz, 1H), 6.37 (s, 2H), 4.62 (dd, J=14.4, 5.7 Hz, 2H), 3.27 (t, J=8.7 Hz, 2H).

<Examples> General Procedure E: Synthesis of Compound 7a-v and Synthesis of Compound 7w

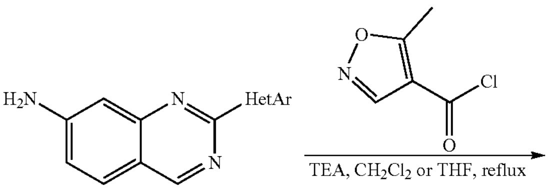

6

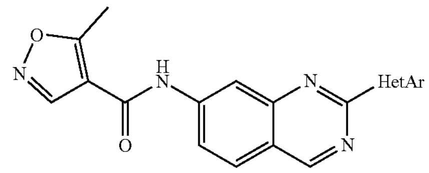

7

5-methylisoxazole-4-carbonyl chloride (1.2 eq-2 eq) and Compound 6 (1 eq) were dissolved in MC or THF (0.1 M), and the resulting solution was stirred at 65° C. After the reaction was completed by consuming as much Compound 6 as possible, the resulting product was cooled at room temperature and distilled under reduced pressure. After layers were separated under weakly basic conditions using EtOAC and a saturated aqueous sodium carbonate solution to remove excess methyl isoxazole, excess moisture was removed using anhydrous $Na_2SO_4$. The resulting product was purified by silica gel column chromatography to obtain final Compound 7.

The following compounds were obtained by the methods of the Examples.

<Example 1> 5-methyl-N-(2-(4-morpholino-5-(trifluoromethyl)phenyl)quinazolin-7-yl)isoxazole-4-carboxamide (7a)

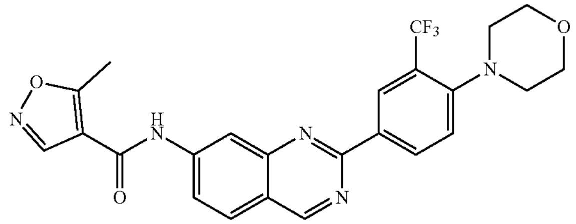 [SMILES: Cc1oncc1C(=O)Nc1ccc2cnc(-c3ccc(N4CCOCC4)c(C(F)(F)F)c3)nc2c1]

The compound was synthesized from Compound 6a using General Procedure E. A target Compound 7a (33%) was obtained as a solid; $^{1}$H NMR (400 MHz DMSO-$d_6$) δ 10.54 (s, 1H), 9.56 (d, J=0.7 Hz, 1H), 9.16 (d, J=0.6 Hz, 1H), 8.82 (d, J=2.0 Hz, 1H), 8.77 (dd, J=8.5, 1.9 Hz, 1H), 8.59 (d, J=1.9 Hz, 1H), 8.15 (d, J=8.8 Hz, 1H), 7.90 (dd, J=8.8, 2.0 Hz, 1H), 7.69 (d, J=8.5 Hz, 1H), 3.79-3.75 (m, 4H), 3.02-2.97 (m, 4H), 2.75 (d, J=0.4 Hz, 3H); $^{13}$C NMR (101 MHz DMSO-$d_6$) δ 173.6, 160.2, 159.9, 158.6, 153.7, 150.9, 149.0, 144.1, 133.6, 132.8, 128.5, 125.5, 125.0, 124.2, 122.8, 121.7, 120.1, 115.0, 111.8, 66.5, 53.2, 12.2; HRMS (ESI$^+$) calculated for $C_{24}H_{20}F_3N_5O_3$ [M+H]$^+$: 484.1518, found 484.4126.

<Example 2> 5-methyl-N-(2-(3-morpholino-5-(trifluoromethyl)phenyl)quinzolin-7-yl)isoxazole-4-carboxamide (7b)

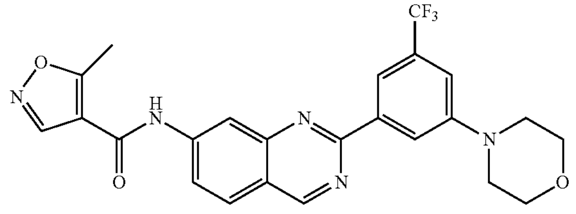 [SMILES: Cc1oncc1C(=O)Nc1ccc2cnc(-c3cc(N4CCOCC4)cc(C(F)(F)F)c3)nc2c1]

The compound was synthesized from Compound 6b using General Procedure E. A target Compound 7b (53%) was obtained as a solid; $^{1}$H NMR (400 MHz, DMSO-$d_6$) δ 10.56 (s, 1H), 9.59 (d, J=0.7 Hz, 1H), 9.16 (d, J=0.6 Hz, 1H), 8.67 (d, J=1.9 Hz, 1H), 8.38 (s, 1H), 8.26 (s, 1H), 8.18 (d, J=8.8 Hz, 1H), 7.90 (dd, J=8.8, 2.0 Hz, 1H), 7.41 (s, 1H), 3.87-3.74 (m, 4H), 3.34 (d, J=4.9 Hz, 4H), 2.74 (s, 3H); $^{13}$C NMR (101 MHz, $CDCl_3$) δ 174.5, 160.2, 160.0, 159.4, 151.7 151.6, 148.1, 143.2, 139.6, 132.0, 131.7, 128.0, 125.7, 121.7, 120.9, 118.2, 116.7, 113.6, 111.9, 66.8, 48.9, 12.8; HRMS (ESI$^+$) calculated for $C_{24}H_{20}F_3N_5O_3$ [M+H]$^+$: 484.1518, found 484.3579.

<Example 3> 5-methyl-N-(2-(3-(4-methyl-1H-imidazol-1-yl)-5-(trifluoromethyl)phenyl)quinazolin-7-yl)isoxazole-4-carboxamide (7c)

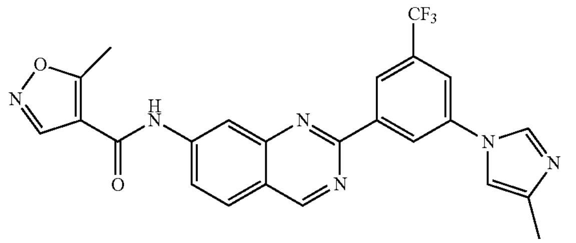 [SMILES: Cc1cn(-c2cc(-c3ncc4ccc(NC(=O)c5cnoc5C)cc4n3)cc(C(F)(F)F)c2)cn1]

The compound was synthesized from Compound 6c using General Procedure E. A target Compound 7c (11%) was obtained as a solid; $^{1}$H NMR (400 MHz, DMSO-$d_6$) δ 10.60 (s, 1H), 9.65 (s, 1H), 9.17 (s, 1H), 8.89 (s, 1H), 8.74 (s, 1H), 8.72 (s, 1H), 8.42 (s, 1H), 8.23 (d, 1H), 8.21 (s, 1H), 7.93 (dd, J=8.8, 1.8 Hz, 1H), 7.73 (s, 1H), 2.75 (s, 3H), 2.21 (s, 3H); $^{13}$C NMR (101 MHz, DMSO-$d_6$) δ 174.2, 161.5, 160.9, 160.5, 160.5, 151.4, 149.6, 149.5, 144.8, 141.0, 139.6, 138.8, 137.3, 137.0, 136.1, 136.1, 123.1, 122.9, 122.8, 122.2, 121.0, 112.3, 67.3, 12.7; HRMS (ESI$^+$) calculated for $C_{24}H_{17}F_3N_6O_2$ [M+H]$^+$: 479.1365, found 479.3079.

<Example 4> 5-methyl-N-(2-(3-(4-methylpiperazin-1-yl)-5-(trifluoromethyl)phenyl)quinazolin-7-yl) isoxazole-4-carboxamide (7d)

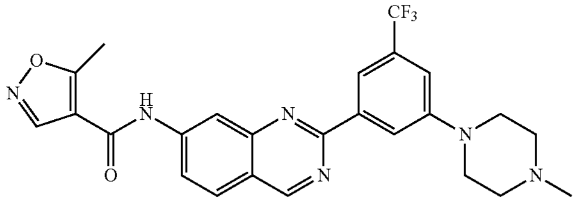 [SMILES: Cc1oncc1C(=O)Nc1ccc2cnc(-c3cc(N4CCN(C)CC4)cc(C(F)(F)F)c3)nc2c1]

The compound was synthesized from Compound 6d using General Procedure E. A target Compound 7d (3%) was obtained as a solid; $^{1}$H NMR (400 MHz, DMSO-$d_6$) δ 10.60 (s, 1H), 9.60 (s, 1H), 9.19 (s, 1H), 8.69 (s, 1H), 8.39 (s, 1H), 8.25 (s, 1H), 8.20 (d, J=8.8 Hz, 1H), 7.93 (dd, J=8.9, 1.9 Hz, 1H), 7.42 (s, 1H), 3.42 (s, 4H), 2.76 (s, 3H), 2.67 (s, 4H), 2.37 (s, 3H); $^{13}$C NMR (101 MHz, DMSO-$d_6$) δ 174.2, 160.6, 160.5, 159.5, 152.0, 151.4, 149.6, 149.6, 144.6, 139.8, 130.8, 129.1, 122.4, 122.4, 120.9, 120.9, 117.8, 115.6, 112.3, 54.6, 47.7, 47.7, 12.8; HRMS (ESI$^+$) calculated for $C_{25}H_{23}F_3N_6O_2$ [M+H]$^+$: 497.1835, found 497.3947.

<Example 5> N-(2-(3-((4-ethylpiperazin-1-yl) methyl)-5-(trifluoromethyl)phenyl)quinazolin-7-yl)-5-methylisoxazole-4-carboxamide (7e)

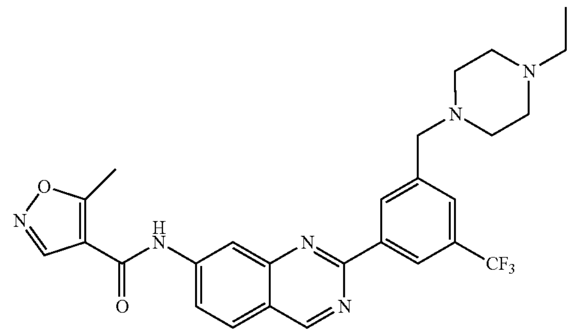 [SMILES: CCN1CCN(Cc2cc(-c3ncc4ccc(NC(=O)c5cnoc5C)cc4n3)cc(C(F)(F)F)c2)CC1]

The compound was synthesized from Compound 6e using General Procedure E. A target Compound 7e (12%) was obtained as a solid; $^1$H NMR (400 MHz, $CDCl_3$) δ 9.38 (s, 1H), 8.80 (s, 1H), 8.73 (s, 2H), 8.32 (s, 2H), 8.02 (d, J=7.6 Hz, 1H), 7.96 (d, J=8.8 Hz, 1H), 7.77 (s, 1H), 3.75 (s, 2H), 2.86 (s, 3H), 2.72 (s, 4H), 2.64 (d, J=7.2 Hz, 2H), 1.97 (s, 4H), 1.19 (d, J=7.2 Hz, 3H); HRMS ($ESI^+$) calculated for $C_{27}H_{27}F_3N_6O_2$ $[M+H]^+$: 525.2148, found 525.6202.

<Example 6> N-(2-(3-fluoro-5-(trifluoromethyl) phenyl)quinazolin-7-yl)-5-methylisoxazole-4-carboxamide (7f)

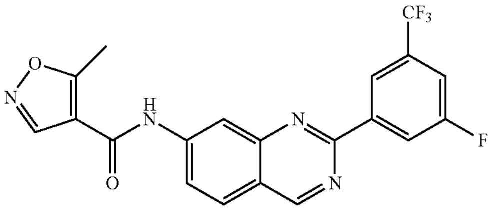 [SMILES: Cc1oncc1C(=O)Nc1ccc2cnc(-c3cc(F)cc(C(F)(F)F)c3)nc2c1]

The compound was synthesized from Compound 6f using General Procedure E. A target Compound 7f (95%) was obtained as a solid; $^1$H NMR (400 MHz, $CDCl_3$) δ 9.34 (s, 1H), 9.15 (s, 1H), 8.93 (s, 1H), 8.72 (s, 1H), 8.50 (d, J=9.9 Hz, 1H), 8.43 (s, 1H), 8.05 (d, J=7.8 Hz, 1H), 7.90 (d, J=8.7 Hz, 1H), 7.46 (d, J=8.0 Hz, 1H), 2.83 (s, 3H); $^{13}$C NMR (101 MHz, $CDCl_3$) δ 174.6, 164.0, 161.6, 160.0, 159.6, 158.6, 151.3, 148.2, 143.6, 141.3, 141.2, 128.1, 122.3, 121.2, 120.9, 118.8, 118.6, 116.5, 111.9, 12.8; HRMS ($ESI^+$) calculated for $C_{20}H_{12}F_4N_4O_2$ $[M+H]^+$: 417.0896, found 417.3687.

<Example 7> N-(2-(4-chloro-3-(trifluoromethyl) phenyl)quinazolin-7-yl)-5-methylisoxazole-4-carboxamide (7g)

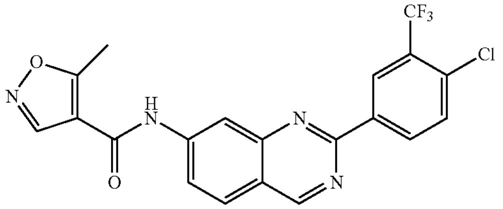 [SMILES: Cc1oncc1C(=O)Nc1ccc2cnc(-c3ccc(Cl)c(C(F)(F)F)c3)nc2c1]

The compound was synthesized from Compound 6g using General Procedure E. A target Compound 7g (80%) was obtained as a solid; $^1$H NMR (400 MHz, DMSO-$d_6$) δ 10.58 (s, 1H), 9.60 (s, 1H), 9.16 (s, 1H), 8.92 (d, J=1.8 Hz, 1H), 8.79 (dd, J=8.4, 1.8 Hz, 1H), 8.62 (d, J=1.6 Hz, 1H), 8.18 (d, J=8.8 Hz, 1H), 7.99-7.88 (m, 2H), 2.74 (s, 3H); $^{13}$C NMR (101 MHz, DMSO-$d_6$) δ 174.2, 170.8, 160.9, 160.5, 151.3, 149.5, 144.8, 137.5, 135.1, 133.6, 133.6, 132.9, 132.9, 132.9, 129.2, 122.7, 120.9, 115.5, 112.3, 12.8; HRMS ($ESI^+$) calculated for $C_{20}H_{12}C_1F_3N_3O_2$ $[M+H]^+$: 433.0601, found 433.1064.

<Example 8> 5-methyl-N-(2-(1-phenyl-5-(trifluoromethyl)-1H-pyrazol-4-yl)quinazolin-7-yl)isoxazole-4-carboxamide (7h)

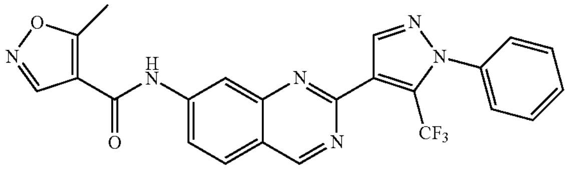 [SMILES: Cc1oncc1C(=O)Nc1ccc2cnc(-c3cnn(-c4ccccc4)c3C(F)(F)F)nc2c1]

The compound was synthesized from Compound 6h using General Procedure E. A target Compound 7h (80%) was obtained as a solid; $^1$H NMR (400 MHz, DMSO-$d_6$) δ 10.57 (s, 1H), 9.58 (d, J=0.7 Hz, 1H), 9.16 (d, J=0.6 Hz, 1H), 8.52 (d, J=2.0 Hz, 1H), 8.49 (s, 1H), 8.18 (d, J=8.8 Hz, 1H), 8.01 (dd, J=8.9, 2.0 Hz, 1H), 7.61 (d, J=7.5 Hz, 5H), 2.78-2.71 (m, 3H); $^{13}$C NMR (101 MHz, DMSO-$d_6$) δ 174.3, 174.2, 163.1, 160.4, 151.3, 151.2, 149.6, 144.7, 142.3, 140.1, 130.2, 129.8, 129.0, 126.4, 125.6, 122.5, 121.7, 120.2, 115.3, 112.2, 12.8; HRMS ($ESI^+$) calculated for $C_{23}H_{15}F_3N_6O_2$ $[M+H]^+$: 465.1209, found 465.3015.

<Example 9> N-(2-(3-chlorophenyl)quinazolin-7-yl)-5-methylisoxazole-4-carboxamide (7i)

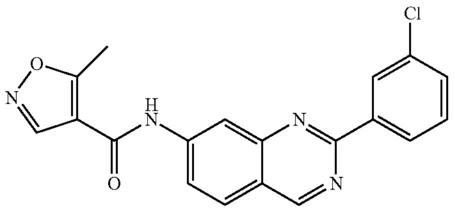 [SMILES: Cc1oncc1C(=O)Nc1ccc2cnc(-c3cccc(Cl)c3)nc2c1]

The compound was synthesized from Compound 6i using General Procedure E. A target Compound 7i (95%) was obtained as a solid; $^{1}$H NMR (400 MHz, DMSO-$d_6$) δ 10.57 (s, 1H), 9.56 (d, J=0.7 Hz, 1H), 9.16 (d, J=0.6 Hz, 1H), 8.59 (d, J=2.0 Hz, 1H), 8.50 (dtd, J=8.3, 2.4, 1.6 Hz, 2H), 8.15 (d, J=8.8 Hz, 1H), 7.92 (dd, J=8.8, 2.0 Hz, 1H), 7.63-7.57 (m, 2H), 2.74 (d, J=0.5 Hz, 3H); $^{13}$C NMR (101 MHz, DMSO-$d_6$) δ 174.1, 170.8, 160.7, 160.4, 159.3, 151.4, 149.6, 144.6, 140.2, 134.1, 131.2, 131.0, 129.0, 128.0, 122.4, 120.8, 115.6, 112.3, 12.7; HRMS (ESI$^+$) calculated for $C_{19}H_{13}ClN_4O_2$ [M+H]$^+$: 365.0727, found 365.6163.

<Example 10> (E)-N-(2-(4-methoxystyryl)quinazolin-7-yl)-5-methylisoxazole-4-carboxamide (7j)

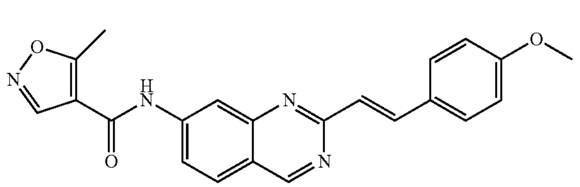 [SMILES: COc1ccc(/C=C/c2ncc3ccc(NC(=O)c4cnoc4C)cc3n2)cc1]

The compound was synthesized from Compound 6j using General Procedure E. A target Compound 7j (95%) was obtained as a solid; $^{1}$H NMR (400 MHz, DMSO-$d_6$) δ 10.54 (s, 1H), 9.44 (s, 1H), 9.16 (d, J=0.6 Hz, 1H), 8.46 (d, J=1.9 Hz, 1H), 8.09 (dd, J=12.4, 8.8 Hz, 2H), 7.88 (dd, J=8.8, 2.0 Hz, 1H), 7.76 (d, J=8.7 Hz, 2H), 7.28 (d, J=16.0 Hz, 1H), 7.03 (d, J=8.8 Hz, 2H), 3.83 (s, 3H), 2.78-2.73 (m, 3H); $^{13}$C NMR (101 MHz, DMSO-$d_6$) δ 174.0, 169.0, 161.8, 160.7, 160.4, 160.0, 151.5, 149.6, 144.2, 138.0, 129.8, 128.9, 126.1, 121.5, 120.2, 115.3, 114.9, 112.4, 55.8, 12.7; HRMS (ESI$^+$) calculated for $C_{22}H_{18}N_4O_3$ [M+H]$^+$: 387.1379, found 387.2971.

<Example 11> (E)-N-(2-(4-chlorostyryl)quinazolin-7-yl)-5-methylisoxazole-4-carboxamide (7k)

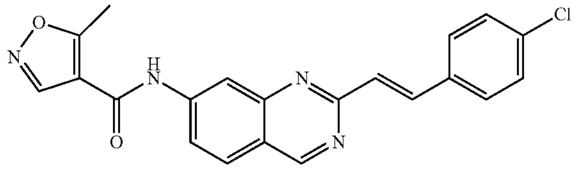 [SMILES: Cc1oncc1C(=O)Nc1ccc2cnc(/C=C/c3ccc(Cl)cc3)nc2c1]

The compound was synthesized from Compound 6k using General Procedure E. A target Compound 7k (73%) was obtained as a solid; $^{1}$H NMR (400 MHz, DMSO-$d_6$) δ 10.54 (s, 1H), 9.46 (s, 1H), 9.14 (d, J=0.6 Hz, 1H), 8.48 (d, J=2.0 Hz, 1H), 8.10 (dd, J=12.4, 9.7 Hz, 2H), 7.89 (dd, J=8.8, 2.0 Hz, 1H), 7.84 (d, J=8.5 Hz, 2H), 7.53-7.47 (m, 2H), 7.43 (d, J=16.0 Hz, 1H), 2.73 (d, J=0.4 Hz, 3H); $^{13}$C NMR (101 MHz, DMSO-$d_6$) δ 174.0, 161.2, 160.4, 160.0, 151.4, 149.5, 144.3, 136.7, 135.2, 134.0, 129.8, 129.4, 129.3, 128.9, 121.8, 120.3, 115.4, 112.3, 12.7; HRMS (ESI$^+$) calculated for $C_{21}H_{15}ClN_4O_2$ [M+H]$^+$: 391.0884, found 397.2947.

<Example 12> N-(2-(5-(tert-butyl)isoxazol-3-yl)quinazolin-7-yl)-5-methylisoxazole-4-carboxamide (7l)

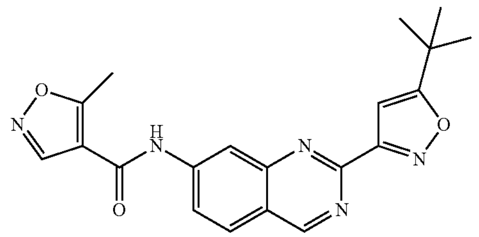 [SMILES: Cc1oncc1C(=O)Nc1ccc2cnc(-c3cc(C(C)(C)C)on3)nc2c1]

The compound was synthesized from Compound 6l using General Procedure E. A target Compound 7l (59%) was obtained as a solid; $^{1}$H NMR (400 MHz, DMSO-$d_6$) δ 10.59 (s, 1H), 9.58 (s, 1H), 9.14 (s, 1H), 8.62 (s, 1H), 8.19 (d, J=8.1 Hz, 1H), 7.95 (d, J=8.0 Hz, 1H), 6.89 (s, 1H), 2.73 (s, 3H), 1.39 (s, 9H); $^{13}$C NMR (101 MHz, $CDCl_3$) δ 182.7, 174.4, 162.7, 160.3, 159.7, 154.6, 151.3, 148.5, 144.5, 128.0, 123.1, 121.2, 116.3, 112.0, 99.0, 33.0, 28.8, 12.8; HRMS (ESI$^+$) calculated for $C_{20}H_{19}N_5O_3$ [M+H]$^+$: 378.1488, found 378.4376.

<Example 13> N-(2-(1H-indazol-5-yl)quinazolin-7-yl)-5-methylisoxazole-4-carboxamide (7m)

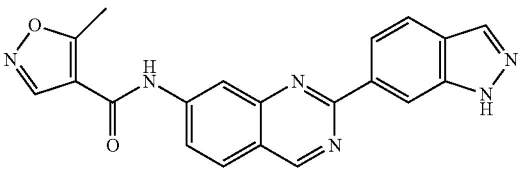 [SMILES: Cc1oncc1C(=O)Nc1ccc2cnc(-c3ccc4cn[nH]c4c3)nc2c1]

The compound was synthesized from Compound 6m using General Procedure E. A target Compound 7m (8%) was obtained as a solid; $^{1}$H NMR (400 MHz, DMSO-$d_6$) δ 13.34 (s, 1H), 10.59 (s, 1H), 9.61 (s, 1H), 9.18 (s, 1H), 8.78 (d, J=0.6 Hz, 1H), 8.62 (d, J=1.5 Hz, 1H), 8.39 (dd, J=8.6, 1.1 Hz, 1H), 8.20-8.15 (m, 2H), 7.97-7.91 (m, 2H), 2.77 (s, 3H); HRMS (ESI$^+$) calculated for $C_{20}H_{14}N_6O_2$ [M+H]$^+$: 371.1178, found 371.4147.

<Example 14> 5-methyl-N-(2-(3-((1-methylpiperidin-4-yl)oxy)-5-(trifluoromethyl)phenyl)quinazolin-7-yl)isoxazole-4-carboxamide (7n)

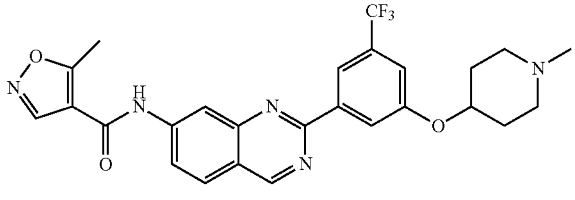 [SMILES: Cc1oncc1C(=O)Nc1ccc2cnc(-c3cc(OC4CCN(C)CC4)cc(C(F)(F)F)c3)nc2c1]

The compound was synthesized from Compound 6n using General Procedure E. A target Compound 7n (4%) was obtained as a solid; $^{1}$H NMR (400 MHz, $CDCl_3$) δ 9.36 (s, 1H), 8.93 (s, 1H), 8.69 (s, 1H), 8.50 (s, 1H), 8.44 (d, J=1.0 Hz, 1H), 8.32 (s, 1H), 8.14 (dd, J=8.6, 1.1 Hz, 1H), 7.98 (d, J=8.9 Hz, 1H), 7.25 (s, 1H), 4.83 (m, 1H), 3.11 (m, 2H), 2.86 (s, 3H), 2.46 (d, J=20.9 Hz, 2H), 2.20 (d, J=8.2 Hz, 2H), 2.06 (d, J=6.9 Hz, 2H), 1.26 (s, 3H); HRMS (ESI$^+$) calculated for $C_{26}H_{24}F_3N_5O_3$ [M+H]$^+$: 512.1831, found 512.6204.

<Example 15> N-(2-(1-acetylpiperidin-4-yl)quinazolin-7-yl)-5-methylisoxazole-4-carboxamide (7o)

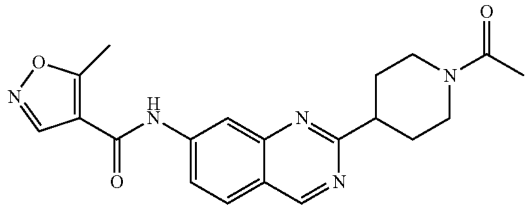 [SMILES: CC(=O)N1CCC(c2ncc3ccc(NC(=O)c4cnoc4C)cc3n2)CC1]

The compound was synthesized from Compound 6o using General Procedure E. A target Compound 7o (30%) was obtained as a solid; $^1$H NMR (400 MHz, DMSO-d$_6$) δ 10.55 (s, 1H), 9.44 (s, 1H), 9.16 (s, 1H), 8.47 (d, J=1.6 Hz, 1H), 8.11 (d, J=8.8 Hz, 1H), 7.90 (dd, J=8.8, 1.9 Hz, 1H), 4.48 (d, J=13.0 Hz, 1H), 3.95 (d, J=13.5 Hz, 1H), 3.28-3.20 (m, 2H), 2.81-2.72 (m, 4H), 2.12-2.01 (m, 5H), 1.86 (ddd, J=16.0, 12.4, 4.2 Hz, 1H), 1.69 (ddd, J=16.1, 12.5, 4.1 Hz, 1H); HRMS (ESL) calculated for $C_{20}H_{21}N_5O_3$ [M+H]$^+$: 380.1644, found 380.5264.

<Example 16> 5-methyl-N-(2-(pyridin-4-yl)quinazolin-7-yl)isoxazole-4-carboxamide (7p)

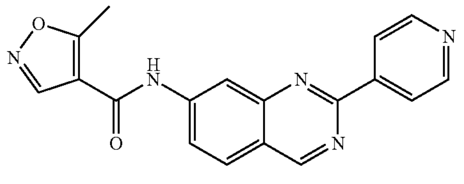 [SMILES: Cc1oncc1C(=O)Nc1ccc2cnc(-c3ccncc3)nc2c1]

The compound was synthesized from Compound 6p using General Procedure E. A target Compound 7p (50%) was obtained as a solid; $^1$H NMR (400 MHz, DMSO-d$_6$) δ 10.65 (s, 1H), 9.67 (s, 1H), 9.19 (s, 1H), 8.83 (d, J=6.0 Hz, 2H), 8.68 (s, 1H), 8.44 (dd, J=4.5, 1.6 Hz, 2H), 8.24 (d, J=8.8 Hz, 1H), 8.01 (dd, J=8.8, 1.9 Hz, 1H), 2.76 (s, 3H); HRMS (ESI$^+$) calculated for $C_{18}H_{13}N_5O_2$ [M+H]$^+$: 332.1069, found 332.3738.

<Example 17> 5-methyl-N-(2-(pyridin-2-yl)quinazolin-7-yl)isoxazole-4-carboxamide (7q)

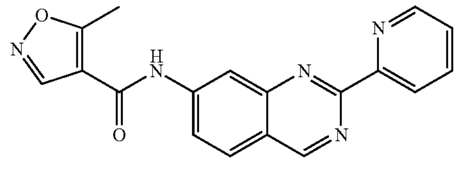 [SMILES: Cc1oncc1C(=O)Nc1ccc2cnc(-c3ccccn3)nc2c1]

The compound was synthesized from Compound 6q using General Procedure E. A target Compound 7q (33%) was obtained as a solid; $^1$H NMR (400 MHz, DMSO-d$_6$) δ 10.59 (s, 1H), 9.61 (s, 1H), 9.15 (s, 1H), 8.79 (d, J=4.1 Hz, 1H), 8.61 (d, J=1.6 Hz, 1H), 8.54 (d, J=7.9 Hz, 1H), 8.19 (d, J=8.8 Hz, 1H), 8.01 (td, J=7.8, 1.7 Hz, 1H), 7.97 (dd, J=8.8, 1.9 Hz, 1H), 7.55 (dd, J=6.6, 4.8 Hz, 1H), 2.74 (s, 3H); $^{13}$C NMR (101 MHz, DMSO-d$_6$) δ 174.0, 160.6, 160.5, 155.4. 151.5, 150.3, 150.1, 149.6, 144.5, 137.7, 128.9, 125.5, 124.4, 122.7, 121.0, 115.8, 112.3; HRMS (ESI$^+$) calculated for $C_{18}H_{13}N_5O_2$ [M+H]$^+$: 332.1069, found 332.5899.

<Example 18> N-(2-(3,4-dichlorophenyl)quinazolin-7-yl)-5-methylisoxazole-4-carboxamide (7r)

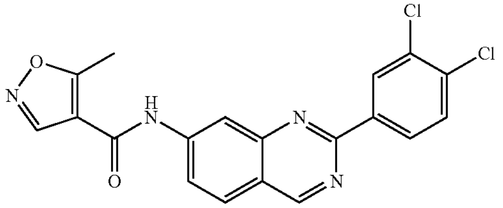 [SMILES: Cc1oncc1C(=O)Nc1ccc2cnc(-c3ccc(Cl)c(Cl)c3)nc2c1]

The compound was synthesized from Compound 6r using General Procedure E. A target Compound 7r (77.3%) was obtained as a solid; $^1$H NMR (400 MHz, $CDCl_3$) δ 9.35 (s, 1H), 8.93 (s, 1H), 8.84 (s, 1H), 8.74 (s, 1H), 8.47 (d, J=8.5 Hz, 1H), 8.41 (s, 1H), 8.03 (d, J=8.0 Hz, 1H), 7.92 (d, J=8.4 Hz, 1H), 7.61 (d, J=8.2 Hz, 1H), 2.84 (s, 3H); $^{13}$C NMR (101 MHz, $CDCl_3$) δ 170.63, 167.28, 166.91, 160.23, 160.18, 159.84, 148.06, 148.01, 130.57, 130.47, 128.12, 128.11, 127.67, 125.26, 123.33, 123.22, 111.87, 102.31, 22.51.

<Example 19> N-(2-(4-fluorobenzyl)quinazolin-7-yl)-5-methylisoxazole-4-carboxamide (7s)

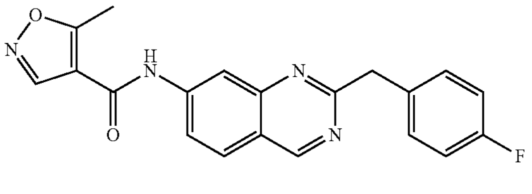 [SMILES: Cc1oncc1C(=O)Nc1ccc2cnc(Cc3ccc(F)cc3)nc2c1]

The compound was synthesized from Compound 6s using General Procedure E. A target Compound 7s (17.8%) was obtained as a solid; $^1$H NMR (400 MHz, DMSO) δ 10.51 (s, 1H), 9.39 (d, J=0.6 Hz, 1H), 9.13 (d, J=0.6 Hz, 1H), 8.44 (d, J=2.0 Hz, 1H), 8.08 (d, J=8.8 Hz, 1H), 7.88 (dd, J=8.8, 2.0 Hz, 1H), 7.44-7.37 (m, 2H), 7.12 (ddd, J=8.9, 5.9, 2.6 Hz, 2H), 4.32 (s, 2H), 2.72 (d, J=0.4 Hz, 3H).

<Example 20> 5-methyl-N-(2-(2-(trifluoromethyl) benzyl)quinazolin-7-yl)isoxazole-4-carboxamide (7t)

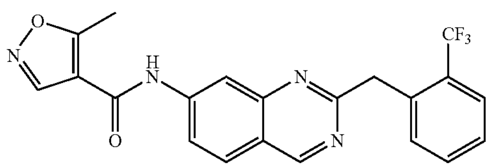 [SMILES: Cc1oncc1C(=O)Nc1ccc2cnc(Cc3ccccc3C(F)(F)F)nc2c1]

The compound was synthesized from Compound 6s using General Procedure E. A target Compound 7t (17.8%) was obtained as a solid; $^1$H NMR (400 MHz, DMSO) δ 10.52 (s, 1H), 9.41 (s, 1H), 9.13 (s, 1H), 8.45 (s, 1H), 8.10 (d, J=8.8 Hz, 1H), 7.91-7.87 (m, 1H), 7.68 (s, 1H), 7.66 (s, 1H), 7.60 (s, 1H), 7.58 (s, 1H), 4.45 (s, 2H), 2.72 (s, 3H).

<Example 21> 5-methyl-N-(2-(naphthalen-2-yl) quinazolin-7-yl)isoxazole-4-carboxamide (7u)

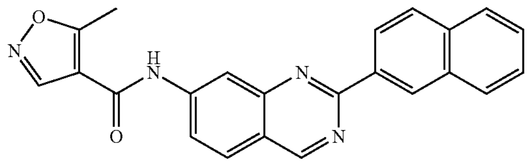 [SMILES: Cc1oncc1C(=O)Nc1ccc2cnc(-c3ccc4ccccc4c3)nc2c1]

The compound was synthesized from Compound 6u using General Procedure E. A target Compound 7u (61%) was obtained as a solid; $^1$H NMR (400 MHz, DMSO) δ 10.58 (s, 1H), 9.62 (d, J=0.7 Hz, 1H), 9.18 (s, 1H), 9.17 (d, J=0.6 Hz, 1H), 8.69 (dd, J=8.7, 1.7 Hz, 1H), 8.67 (d, J=1.9 Hz, 1H), 8.18 (d, J=8.7 Hz, 2H), 8.09 (d, J=8.8 Hz, 1H), 8.01 (dd, J=6.1, 3.2 Hz, 1H), 7.91 (dd, J=8.8, 2.0 Hz, 1H), 7.64-7.57 (m, 2H), 2.76 (s, 3H); $^{13}$C NMR (101 MHz, DMSO) δ 173.56, 160.16, 160.01, 159.92, 151.04, 149.05, 143.92, 134.95, 134.16, 132.87, 129.10, 128.46, 128.32, 128.17, 127.60, 127.34, 126.51, 124.96, 121.51, 120.16, 115.12, 111.82, 12.24.

<Example 22> N-(2-(2,3-dihydrobenzofuran-5-yl) quinazolin-7-yl)-5-methylisoxazole-4-carboxamide (7v)

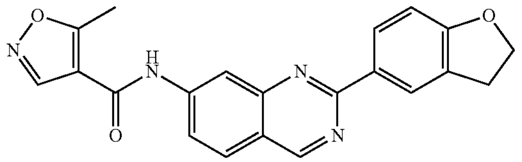 [SMILES: Cc1oncc1C(=O)Nc1ccc2cnc(-c3ccc4c(c3)CCO4)nc2c1]

The compound was synthesized from Compound 6v using General Procedure E. A target Compound 7v (99.2%) was obtained as a solid; $^1$H NMR (400 MHz, DMSO) δ 10.52 (s, 1H), 9.48 (d, J=0.7 Hz, 1H), 9.15 (d, J=0.6 Hz, 1H), 8.51 (d, J=2.0 Hz, 1H), 8.45 (d, J=1.4 Hz, 1H), 8.37 (dd, J=8.4, 1.9 Hz, 1H), 8.09 (d, J=8.8 Hz, 1H), 7.85 (dd, J=8.8, 2.0 Hz, 1H), 6.92 (d, J=8.4 Hz, 1H), 4.64 (t, J=8.8 Hz, 2H), 3.31-3.27 (m, 2H), 2.74 (d, J=0.5 Hz, 3H).

<Example 23> N-(2-(4-methoxyphenethyl)quinazolin-7-yl)-5-methylisoxazole-4-carboxamide (7w)

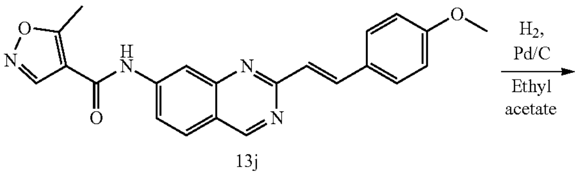

13j

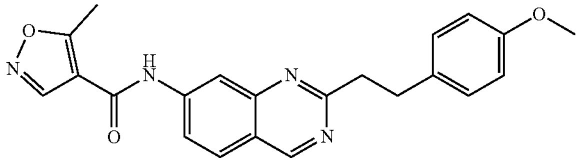

13w

After Compound 7j (1 eq) and Pd/C (10 wt %) were dissolved in ethyl acetate (5 ml), the resulting solution was stirred at room temperature in the presence of hydrogen gas for 40 minutes. After the reaction was completed, the resulting product was filtered with Celite and then distilled under reduced pressure. Compound 7w (57.3%) was obtained from the residue without further purification; $^1$H NMR (400 MHz, DMSO) δ 10.52 (s, 1H), 9.42 (s, 1H), 9.15 (s, 1H), 8.44 (d, J=1.7 Hz, 1H), 8.10 (d, J=8.8 Hz, 1H), 7.89 (dd, J=8.8, 2.0 Hz, 1H), 7.19 (d, J=8.6 Hz, 2H), 6.83 (d, J=8.6 Hz, 2H), 3.71 (s, 3H), 3.28 (dd, J=9.1, 6.7 Hz, 2H), 3.14 (t, J=7.7 Hz, 2H), 2.74 (s, 3H).

Experimental Example 1. Measurement of FLT3 and FLT Enzyme Activity

Changes in FLT3 and FLT enzyme activities by treatment with the quinazoline derivatives of the following Table 1 according to the present invention were confirmed by $IC_{50}$.

TABLE 1

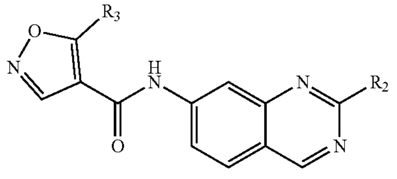

| Example | No | $R_2$ | FLT3 | FLT (ITD) |
|---|---|---|---|---|
| | | | $IC_{50}$ (μM) | |
| 1 | 7a | 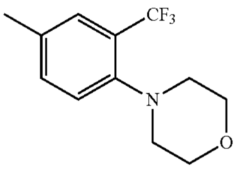 | + | + |

TABLE 1-continued
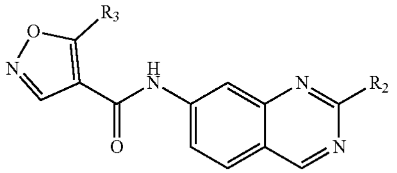
| Example | No | $R_2$ | FLT3 $IC_{50}$ (μM) | FLT (ITD) $IC_{50}$ (μM) |
|---|---|---|---|---|
| 2 | 7b | 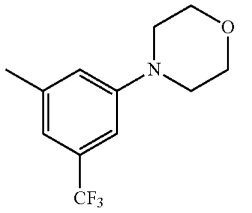 | ++ | ++ |
| 3 | 7c | 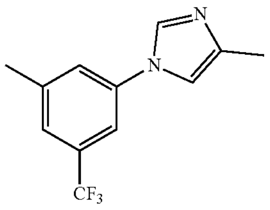 | +++ | +++ |
| 4 | 7d | 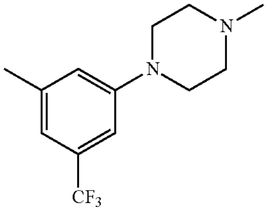 | +++ | +++ |
| 5 | 7e | 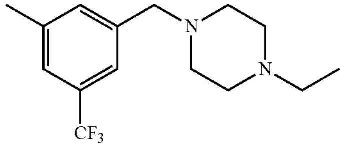 | +++ | ++ |
| 6 | 7f | 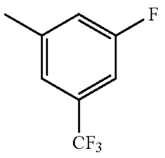 | + | + |
| 7 | 7g | 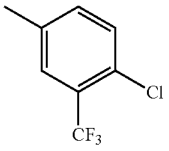 | + | + |
| 8 | 7h | 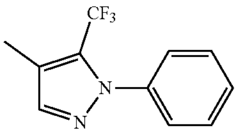 | + | + |
TABLE 1-continued
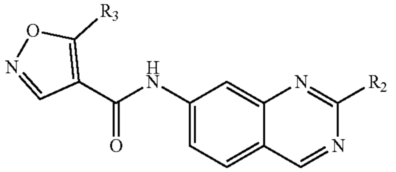
| Example | No | $R_2$ | FLT3 $IC_{50}$ (μM) | FLT (ITD) $IC_{50}$ (μM) |
|---|---|---|---|---|
| 9 | 7i | 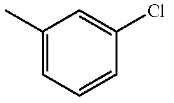 | + | + |
| 10 | 7j | 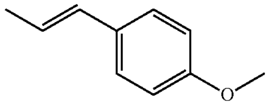 | ++ | + |
| 11 | 7k | 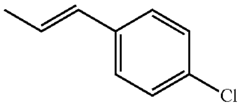 | + | + |
| 12 | 7l | 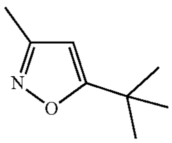 | + | + |
| 13 | 7m | 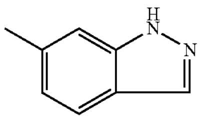 | +++ | +++ |
| 14 | 7n | 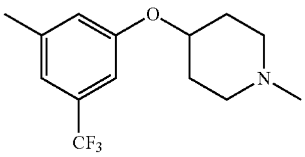 | ++ | ++ |
| 15 | 7o | 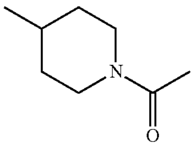 | + | + |
| 16 | 7p | 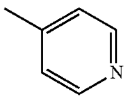 | + | + |
| 17 | 7q | 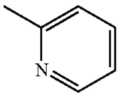 | + | + |
| 18 | 7r | 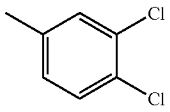 | + | + |

TABLE 1-continued

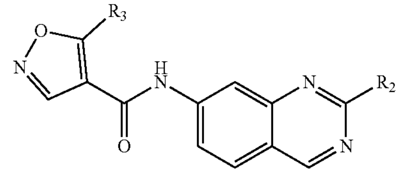

| Example | No | $R_2$ | FLT3 | FLT (ITD) |
|---|---|---|---|---|
| | | | $IC_{50}$ (μM) | |
| 19 | 7s | 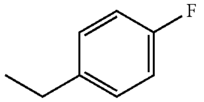 | + | + |
| 20 | 7t | 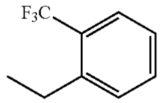 | + | + |
| 21 | 7u | 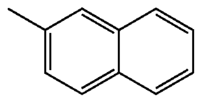 | + | + |
| 22 | 7v | 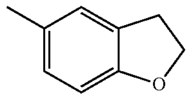 | + | + |
| 23 | 7w | 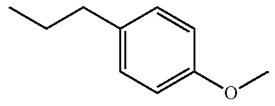 | + | + |

+: when $IC_{50}$ value >10 μM

++: when $IC_{50}$ value is 3 to 10 μM

+++: when $IC_{50}$ value <3 μM

The results of evaluating the FLT3 and FLT-ITD kinase activities of all the quinazoline compounds 7a to 7w are shown in Table 1. Among the synthesized derivatives, particularly, compounds containing a piperazine structure showed selective activity against FLT3. Among them, Compound 7d showed an activity of $IC_{50}$=106 nM against FLT3 and $IC_{50}$=301 nM against FLT-ITD.

Experimental Example 2. Measurement of Inhibitory Activity Against Various Protein Kinases Subsequently, the inhibitory activity of Compound 7d against other different FLT3 mutants was additionally investigated and is shown in Table 2. Referring to the results of the insertion of 1 amino acid sequence ($IC_{50}$ value: 0.524 μM), 2 amino acid sequences ($IC_{50}$ value: 0.495 μM) and 9 amino acid sequences ($IC_{50}$ value: 0.728 μM), the compound strongly suppressed the mutants regardless of sequence and position. Further, Compound 7d was also strong against FLT3 mutations located in the TKD. Compound 7d suppressed FLT3 (D835Y) at $IC_{50}$=228n.

A tyrosine kinase inhibitor was allowed to bind to the ATP-binding site. However, well-known FLT3 mutations such as ITDs and point mutations (TKD) were found on the opposite side of the tyrosine kinase except for the ATP binding site. Therefore, it showed only inhibitory activity similar to that of FLT3 against FLT3-ITD and TKD.

Next, kinase panel screening for Compound 7d was investigated for 36 different kinases at a single dose of 10 μM (FIG. 1 and Table 3).

Compound 7d exhibited an inhibitory activity of 96.6% in FLT3 and 95.2% in FLT-ITD, and Compound 7d also maintained selectivity for FMS. In particular, the quinazoline compound 7d exhibited a selectivity profile compared to cKIT because the compound did not exhibit inhibitory activity against cKIT. The high selectivity against cKIT may be an opportunity to avoid myelosuppressive toxicity reported for dual FLT3/cKIT kinase inhibitors.

Since FLT3 belongs to the same type III receptor tyrosine kinase family having FLT3, it is a very valuable result to secure such a kinase selectivity profile considering that it is difficult to achieve selectivity compared to cKIT and FMS kinases.

TABLE 2

| Kinase | IC50 (μM) |
|---|---|
| FLT3 (F594_R595 ins R) | 0.524 |
| FLT3 (F594_R595 ins EY) | 0.495 |
| FLT3 (Y591_V592 ins VDFREYEYD) | 0.728 |
| FLT3 (D835Y) | 0.228 |

TABLE 3

| Kinase | % inhibition rate | Staurosporine $IC_{50}$ (nM) |
|---|---|---|
| ABL1 | 6.46 | 31.0 |
| AKT1 | 5.48 | 1.98 |
| ALK | 17.0 | 2.35 |
| Aurora A | 20.1 | 0.502 |
| AXL | 21.2 | 3.88 |
| AXL (R499C) | 10.1 | 3.21 |
| BRAF (V599E) | 5.19 | 6.79[a] |
| BTK | 17.5 | 11.7 |
| c-Kit | 0 | 1.40 1 |
| c-MET | 13.2 | 57.8 |
| c-Src | 14.6 | 1.20 |
| CAMKK1 | 0 | 59.6 |
| CDK4/cyclin D1 | 3.01 | 30.4 |
| EGFR | 0 | 65.5 |
| ERK1 | 15.0 | 4.47[b] |
| FGFR3 | 1.00 | 8.87 |
| FLT1/VEGFR1 | 5.23 | 5.65 |
| FLT3 | 96.6 | 1.13 |
| FLT3-ITD | 95.2 | 1.58 |
| FMS | 5.49 | 1.34 |
| FYN | 19.0 | 1.07 |
| GSK3b | 8.06 | 4.4 |
| IGF1R | 00 | 31.7 |
| JAK3 | 0.80 | 0.0784 |
| JNK3 | 19.5 | 65.8[c] |
| KDR/VEGFR2 | 16.8 | 11.4 |
| LCK | 19.7 | 1.39 |
| LYN | 20.5 | 0.675 |
| MEK1 | 0 | 14.7 |
| P38a/MAPK14 | 0 | 16.0[d] |
| PKA | 2.5 | 1.37 |
| PLK1 | 0 | 111 |
| RIPK3 | 12.8 | 1650[a] |
| RON/MST1R | 13.5 | 140 |
| ROS/ROS1 | 14.4 | 0.174 |
| SYK | 22.4 | 0.436 |

[a]Data of GW5074[18]

[b]Data of SCH772984[19,20]

[c]Data of JNKI VIII[21, 22]

[d]Data of SB202190[23]

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described embodiments are only exemplary in all aspects and are not restrictive.

The invention claimed is:

1. A compound of the following Chemical Formula 7 or a pharmaceutically acceptable salt thereof:

[Chemical Formula 7]

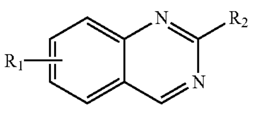

wherein, in Chemical Formula 7, $R_1$ is

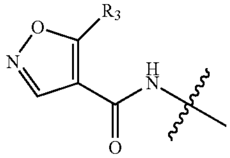

, $R_2$ is selected from the group consisting of indazolyl, naphthalenyl, dihydrobenzofuranyl, pyridinyl, acetyl piperidine, phenyl which is unsubstituted or substituted with one or more non-hydrogen substituents, pyrazolyl which is unsubstituted or substituted with one or more non-hydrogen substituents, dihydroisoxazole which is unsubstituted or substituted with one or more non-hydrogen substituents,

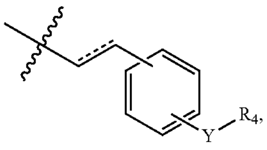

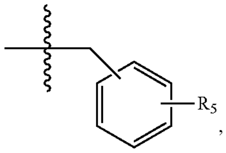

, or a $C_3$-$C_7$ cycloalkyl, the non-hydrogen substituent in $R_2$ is selected from the group consisting of

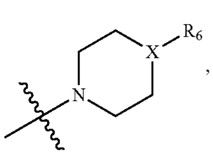

,

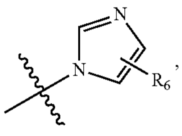

,

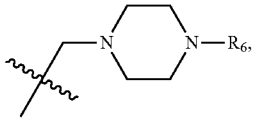

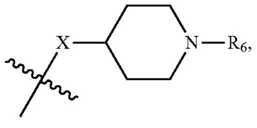

phenyl, hydroxy, a $C_1$-$C_6$ alkyl, a $C_1$-$C_6$ halogenated alkyl, or a halogen atom, $R_3$ is a hydrogen atom, hydroxy, a $C_1$-$C_6$ alkyl or a $C_1$-$C_6$ halogenated alkyl, $R_4$ is a hydrogen atom, hydroxy or a $C_1$-$C_6$ alkyl, or is absent, here, X is a nitrogen or oxygen atom, and Y is a halogen or oxygen atom, $R_5$ is a hydrogen atom, hydroxy, a halogen atom or a $C_1$-$C_6$ halogenated alkyl, $R_6$ is a hydrogen atom, hydroxy or a $C_1$-$C_6$ alkyl, and a connecting line expressed as a double line ( ) of a solid line and a dotted line represents a single carbon-carbon bond or a double carbon-carbon bond.

2. The compound of claim 1, wherein the compound of Chemical Formula 7 has a structure of the following Chemical Formula 7',

[Chemical Formula 7']

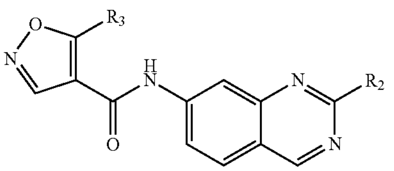

in Chemical Formula 7', $R_2$ is selected from the group consisting of indazolyl, naphthalenyl, dihydrobenzofuranyl, pyridinyl, acetyl piperidine, phenyl which is unsubstituted or substituted with one or more non-hydrogen substituents, pyrazolyl which is unsubstituted or substituted with one or more non-hydrogen substituents, dihydroisoxazole which is unsubstituted or substituted with one or more non-hydrogen substituents,

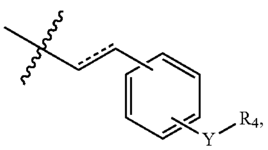

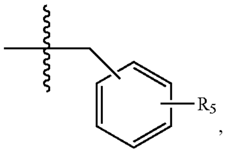

, or a $C_3$-$C_7$ cycloalkyl, the non-hydrogen substituent in R2 is selected from the group consisting of

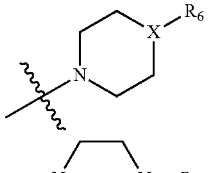

,

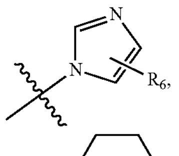

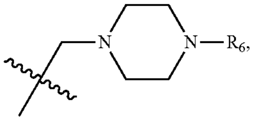

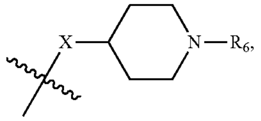

phenyl, hydroxy, a $C_1$-$C_6$ alkyl, a $C_1$-$C_6$ halogenated alkyl, or a halogen atom, $R_3$ is a hydrogen atom, hydroxy, a $C_1$-$C_6$ alkyl or a $C_1$-$C_6$ halogenated alkyl, $R_4$ is a hydrogen atom, hydroxy or a $C_1$-$C_6$ alkyl, or is absent, here, X is a nitrogen or oxygen atom, and Y is a halogen or oxygen atom, $R_5$ is a hydrogen atom, hydroxy, a halogen atom or a $C_1$-$C_6$ halogenated alkyl, $R_6$ is a hydrogen atom, hydroxy or a $C_1$-$C_6$ alkyl, and a connecting line expressed as a double line (z,25 ) of a solid line and a dotted line represents a single carbon-carbon bond or a double carbon-carbon bond.

3. The compound of claim 2, wherein $R_2$ is selected from the group consisting of indazolyl, pyridinyl, phenyl which is unsubstituted or substituted with one or more non-hydrogen substituents, or

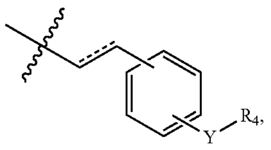

the non-hydrogen substituent in $R_2$ is selected from the group consisting of

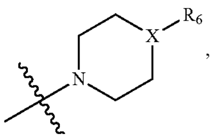,
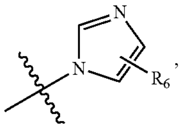,
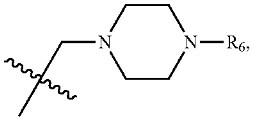,
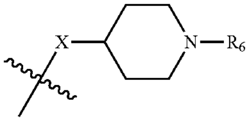

or a $C_1$-$C_6$ halogenated alkyl, $R_3$ is a $C_1$-$C_6$ alkyl, $R_4$ is a $C_1$-$C_6$ alkyl or absent, here, X is an oxygen atom, Y is a halogen or oxygen atom, and $R_6$ is hydrogen or a $C_1$-$C_6$ alkyl, and a connecting line expressed as a double line ( ------ ) of a solid line and a dotted line represents a single carbon-carbon bond or a double carbon-carbon bond.

4. The compound of claim 1, wherein $R_3$ is a $C_1$-$C_6$ alkyl.

5. The compound of claim 1, wherein $R_2$ is

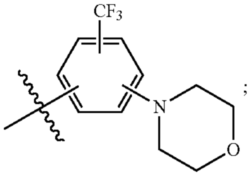;
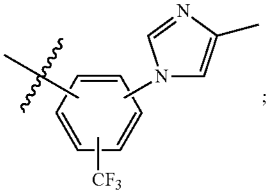;
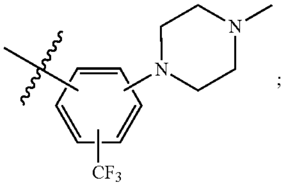;
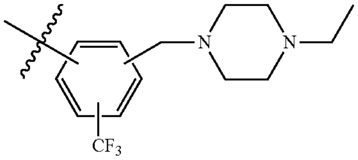;
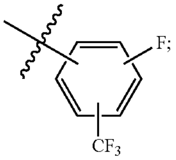
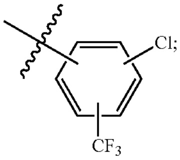

-continued

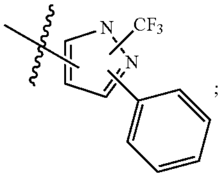;
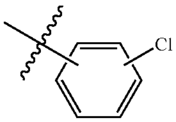;
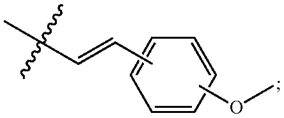
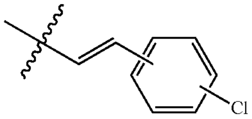;
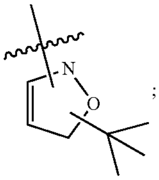;
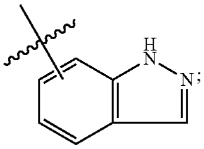
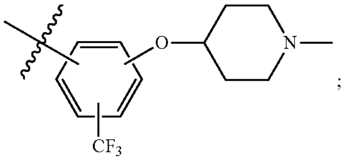;
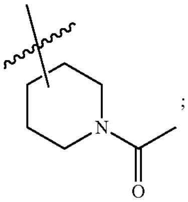;
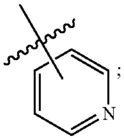;
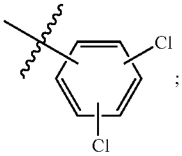
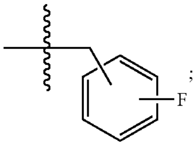;
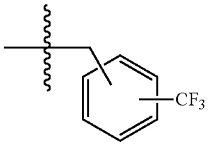;
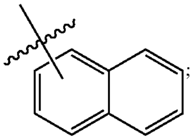;
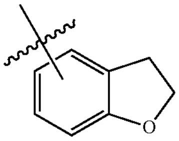
or
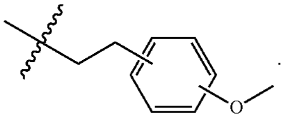.

6. The compound of claim 2, wherein $R_3$ is a $C_1$-$C_6$ alkyl, and $R_2$ is

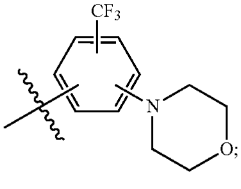
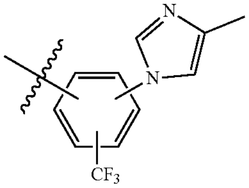;

-continued

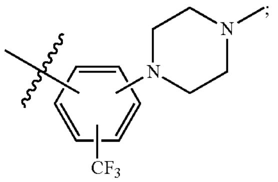

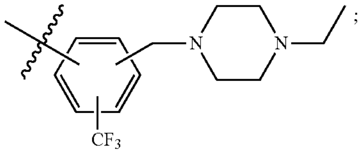

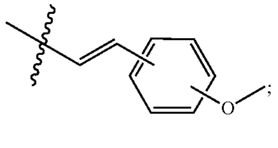

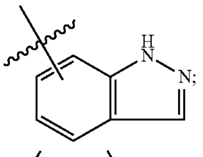

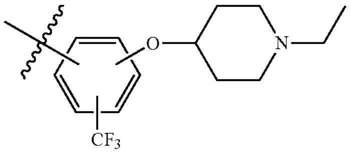

or

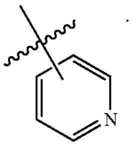

7. The compound of claim 1, wherein the compound of Chemical Formula 7 is 5-methyl-N-(2-(4-morpholino-5-(trifluoromethyl)phenyl) quinazolin-7-yl)isoxazole-4-carboxamide;

5-methyl-N-(2-(3-morpholino-5-(trifluoromethyl)phenyl) quinazolin-7-yl)isoxazole-4-carboxamide;

5-methyl-N-(2-(3-(4-methyl-1H-imidazol-1-yl)-5-(trifluoromethyl)phenyl)quinazolin -7-yl)isoxazole-4-carboxamide;

5-methyl-N-(2-(3-(4-methylpiperazin-1-yl)-5-(trifluoromethyl)phenyl)quinazolin-7-yl)isoxazole-4-carboxamide;

N-(2-(3-((4-ethylpiperazin-1-yl)methyl)-5-(trifluoromethyl)phenyl)quinazolin-7-yl) -5-methylisoxazole-4-carboxamide;

N-(2-(3-fluoro-5-(trifluoromethyl)phenyl)quinazolin-7-yl)-5-methylisoxazole-4-carboxamide;

N-(2-(4-chloro-3-(trifluoromethyl)phenyl)quinazolin-7-yl)-5-methylisoxazole-4-carboxamide;

5-methyl-N-(2-(1-phenyl-5-(trifluoromethyl)-1H-pyrazol-4-yl)quinazolin-7-yl)isoxazole-4-carboxamide;

N-(2-(3-chlorophenyl) quinazolin-7-yl)-5-methylisoxazole-4-carboxamide;

(E)-N-(2-(4-methoxystyryl)quinazolin-7-yl)-5-methylisoxazole-4-carboxamide;

(E)-N-(2-(4-chlorostyryl)quinazolin-7-yl)-5-memthylisoxazole-4-carboxamide;

N-(2-(5-(tert-butyl)isoxazol-3-yl)quinazolin-7-yl)-5-methylisoxazole-4-carboxamide;

N-(2-(1H-indazol-5-yl)quinazolin-7-yl)-5-methylisoxazole-4-carboxamide;

5-methyl-N-(2-(3-((1-methylpiperidin-4-yl)oxy)-5-(trifluoromethyl)phenyl)quinazolin-7-yl)isoxazole-4-carboxamide;

N-(2-(1-acetylpiperidin-4-yl)quinazolin-7-yl)-5-methylisoxazole-4-carboxamide;

5-methyl-N-(2-(pyridin-4-yl)quinazolin-7-yl)isoxazole-4-carboxamide;

5-methyl-N-(2-(pyridin-2-yl)quinazolin-7-yl)isoxazole-4-carboxamide;

N-(2-(3,4-dichlorophenyl)quinazolin-7-yl)-5-methylisoxazole-4-carboxamide;

N-(2-(4-fluorobenzyl)quinazolin-7-yl)-5-methylisoxazole-4-carboxamide;

5-methyl-N-(2-(2-(trifluoromethyl)benzyl)quinazolin-7-yl)isoxazole-4-carboxamide;

5-methyl-N-(2-(naphthalen-2-yl)quinazolin-7-yl)isoxazole-4-carboxamide;

N-(2-(2,3-dihydrobenzofuran-5-yl)quinazolin-7-yl)-5-methylisoxazole-4-carboxamide; or N-(2-(4-methoxyphenethyl)quinazolin-7-yl)-5-methylisoxazole-4-carboxamide.

8. A pharmaceutical composition for preventing or treating cancer, comprising the quinazoline derivative, or the pharmaceutically acceptable salt thereof according to claim 1 as an active ingredient.

9. The pharmaceutical composition of claim 8, wherein the cancer disease is acute myeloid leukemia (AML).

10. The pharmaceutical composition of claim 9, wherein the composition inhibits fms-like tyrosine kinase 3 (FLT 3) activity.

11. A method of treating or preventing cancer in a subject in need thereof, comprising administering to the subject a therapeutically effective amount of the quinazoline derivative, or the pharmaceutically acceptable salt thereof according to claim 1.

12. The method of claim 11, wherein the cancer disease is acute myeloid leukemia (AML).

13. The method of claim 12, wherein the quinazoline derivative inhibits fms-like tyrosine kinase 3 (FLT 3) activity.

* * * * *